US010444129B2

(12) United States Patent
Brown et al.

(10) Patent No.: US 10,444,129 B2
(45) Date of Patent: Oct. 15, 2019

(54) SYSTEM AND METHOD FOR TESTING OR CALIBRATING A MANUFACTURED PART IN A WET ENVIRONMENT

(71) Applicant: ATS AUTOMATION TOOLING SYSTEMS INC., Cambridge (CA)

(72) Inventors: Theodore Robert Brown, Birmingham, MI (US); John Graham, Sterling Heights, MI (US)

( * ) Notice: Subject to any disclaimer, the term of this patent is extended or adjusted under 35 U.S.C. 154(b) by 119 days.

(21) Appl. No.: 15/547,889

(22) PCT Filed: Feb. 4, 2016

(86) PCT No.: PCT/CA2016/050101
§ 371 (c)(1),
(2) Date: Aug. 1, 2017

(87) PCT Pub. No.: WO2016/123713
PCT Pub. Date: Aug. 11, 2016

(65) Prior Publication Data
US 2018/0024034 A1  Jan. 25, 2018

Related U.S. Application Data

(60) Provisional application No. 62/111,767, filed on Feb. 4, 2015.

(51) Int. Cl.
*G01L 5/00* (2006.01)
*G01N 3/12* (2006.01)
*G01N 3/04* (2006.01)

(52) U.S. Cl.
CPC ................. *G01N 3/12* (2013.01); *G01N 3/04* (2013.01); *G01L 5/0076* (2013.01);
(Continued)

(58) Field of Classification Search
CPC .......... G01M 3/329; G01M 3/04; G01M 3/26; G01M 3/02; G01M 3/3236; G01M 3/025;
(Continued)

(56) References Cited

U.S. PATENT DOCUMENTS 5,899,216 A * 5/1999 Goudie ............. H01L 21/67028
134/134
6,213,853 B1 * 4/2001 Gonzalez-Martin .... B24B 37/04
451/287
(Continued)

FOREIGN PATENT DOCUMENTS

CA     2635505      6/2009

OTHER PUBLICATIONS

Canadian Intellectual Property Office as International Searching Authority, International Search Report and Written Opinion on PCT Patent Appln. No. PCT/CA2016/050101, dated Mar. 22, 2016.

*Primary Examiner* — Brandi N Hopkins
(74) *Attorney, Agent, or Firm* — Gowling WLG (Canada) LLP; Neil W. Henderson

(57) ABSTRACT

A system for testing or calibrating a part, the system including: a plurality of test stations, each test station including a container and a clamping mechanism, wherein the clamping mechanism includes: a clamp frame including: two clamp plates; a plurality of clamp bars configured to securely hold the clamp plates at a distance relative to each other; a seal manifold provided on one of the two clamp plates; and a clamping module, located opposite the seal manifold on another of the two clamp plates, wherein the clamping module includes: a plurality of pistons to hold the part against the seal manifold for the test operation; and at least one cleaning station comprising a spin mechanism for spinning the part to remove excess fluid; and a robotic system for moving individual parts to and from the plurality (Continued)

of test stations and to and from the at least one cleaning station.

18 Claims, 31 Drawing Sheets

(52) U.S. Cl.
CPC ............... *G01N 2203/0048* (2013.01); *G01N 2203/0242* (2013.01); *G01N 2203/0405* (2013.01); *G01N 2203/0411* (2013.01)

(58) Field of Classification Search
CPC ..... G01M 3/3281; B23P 19/001; B23P 21/00; B23P 23/04; B23P 19/042; B23P 21/002; B23P 2700/50; G05B 19/418; G05B 19/41805; G05B 2219/31054; Y02P 90/28; Y02P 90/04
See application file for complete search history.

(56) References Cited

U.S. PATENT DOCUMENTS

| | | | |
|---|---|---|---|
| 6,463,969 B1 * | 10/2002 | Devlin, Sr. ........... | B01L 3/0293 141/130 |
| 8,229,586 B2 * | 7/2012 | Wallace ................ | B23P 19/001 700/111 |
| 2013/0031961 A1 | 2/2013 | Nandwani et al. | |
| 2013/0031962 A1 | 2/2013 | Nandwani et al. | |

\* cited by examiner

SYSTEM AND METHOD FOR TESTING OR CALIBRATING A MANUFACTURED PART IN A WET ENVIRONMENT

RELATED APPLICATIONS

This patent disclosure claims the benefit of U.S. Provisional Patent No. 62/111,767 filed Feb. 4, 2015, the content of which is hereby incorporated herein by reference.

FIELD

The present document relates to a system and method for testing and/or calibration in a pressurized and/or wet environment, particularly for parts that must be tested using fluids and pressure is needed on the part for the testing and/or calibration, or the like.

BACKGROUND

Existing systems for testing or calibrating use various techniques to allow for the testing or calibration depending on the nature of the parts. Two instances where testing and calibration become more complex include: (1) those where some element of the part to be tested needs to be placed under pressure during testing; and (2) those where the testing or calibration process makes use of a liquid and the liquid is ideally removed prior to moving the part to another processing operation. One example of where these two conditions apply is the testing and calibration of a transmission control apparatus. In this process, a part is submerged in oil and requires a predetermined amount of pressure to be placed on bolt locations where the part would be attached when in use.

Current systems and methods for testing and calibration can be complex and costly in order to meet these requirements. For example, when testing a transmission control apparatus, a large press is conventionally used to provide the necessary pressure to the transmission control apparatus. As another example, in some "wet" testing/calibration processes, the part may be air-dried following the testing. However, air drying can release mist which may require a complex mist collection mechanism to prevent spread of the mist into other areas. A mist can be particularly problematic when it is formed from an oil that was used in the process.

There is a need for an improved system and method for testing and/or calibration in a pressurized and/or wet environment.

SUMMARY

In a first aspect, the present disclosure provides a system for testing or calibrating a part, the system including: a plurality of test stations, each test station comprising a container and a clamping mechanism, wherein the container is configured to hold a fluid and the clamping mechanism is configured to receive the part in a vertical orientation and clamp the part horizontally with sufficient force to withstand a predetermined pressure to be placed on the part while submerged in the fluid, wherein the clamping mechanism includes: a clamp frame including: two clamp plates; a plurality of clamp bars configured to securely hold the clamp plates at a distance relative to each other; a seal manifold provided on one of the two clamp plates; and a clamping module, located opposite the seal manifold on another of the two clamp plates, wherein the clamping module includes: a plurality of pistons to hold the part against the seal manifold for the test operation; and at least one cleaning station comprising a spin mechanism for spinning the part to remove excess fluid; and a robotic system for moving individual parts to and from the plurality of test stations and to and from the at least one cleaning station.

In a particular case, the robotic system may include: a gantry located above the plurality of test stations; a robotic module comprising: at least one moving mechanism configured to move along the gantry; and a robot gripper attached to each moving mechanism and configured to grip and transport the part.

In another particular case, the robot gripper may be configured to maintain the vertical orientation of the part.

In still another particular case, the system may include a pallet for carrying the part and wherein the robot gripper includes a lock/release mechanism configured to interact with the pallet.

In yet another particular case, the robotic system may include: a floor mount; and a robotic arm attached to the floor mount, wherein the robotic arm moves the part to and from the plurality of test stations.

In a particular case, the spinning mechanism may maintain the part in a vertical orientation.

In another particular case, the system may include: a plurality of test panels, wherein each of the plurality of test panels engage with one of the plurality of test stations such that each of the engaged test panels and test stations can be slidably removed from the system.

In another aspect, there is provided a method for testing or calibrating a part, the method including: receiving the part from a conveyor; transporting the part to a test station while orienting the part in a vertical orientation; inserting the part in a clamping mechanism in the test station while maintaining the part in a vertical orientation; applying pressure to the part via the clamping mechanism, wherein the pressure is applied in a horizontal direction; testing the part, while maintaining the part in a vertical orientation and while under pressure; releasing the pressure and removing the part from the clamping mechanism; and returning the part to the conveyor.

In a particular case, the test station includes a fluid and the part is tested in a fluid, the method further comprising cleaning the part at a cleaning station by spinning the part to remove excess fluid.

In still yet another aspect, there is provided a system for testing or calibrating parts under pressure, the system including: a plurality of test stations, each test station comprising: a clamping mechanism configured to receive the part in a vertical orientation and clamp the part horizontally with sufficient force to withstand a predetermined pressure to be placed on the part; and a robotic system for moving individual parts to and from the plurality of test stations.

In a particular case, the clamping mechanism may include: a clamp frame including: two clamp plates; a plurality of clamp bars configured to securely hold the clamp plates at a distance relative to each other; a seal manifold provided on one of the two clamp plates; and a clamping module, located opposite the seal manifold on another of the two clamp plates, wherein the clamping module includes: a plurality of pistons to hold the part against the seal manifold for the test operation.

In still another particular case, the robotic system may include: a gantry located above the plurality of test stations; a robotic module including: at least one moving mechanism configured to move along the gantry; and a robot gripper attached to each moving mechanism and configured to grip and transport the part.

In yet another particular case, the robot gripper may be configured to maintain the vertical orientation of the part.

In still yet another particular case, the system may include a pallet for carrying the part and wherein the robot gripper includes a lock/release mechanism configured to interact with the pallet.

In a particular case, the robotic system may include: a floor mount; and a robotic arm attached to the floor mount, wherein the robotic arm moves the part to and from the plurality of test stations.

In another particular case, the system may include at least one cleaning station comprising a spin mechanism for spinning.

In still another particular case, the spinning mechanism maintains the part in a vertical orientation.

In still yet another particular case, the system may further include: a plurality of test panels, wherein each of the plurality of test panels engage with one of the plurality of test stations such that each of the engaged test panels and test stations can be slidably removed from the system.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
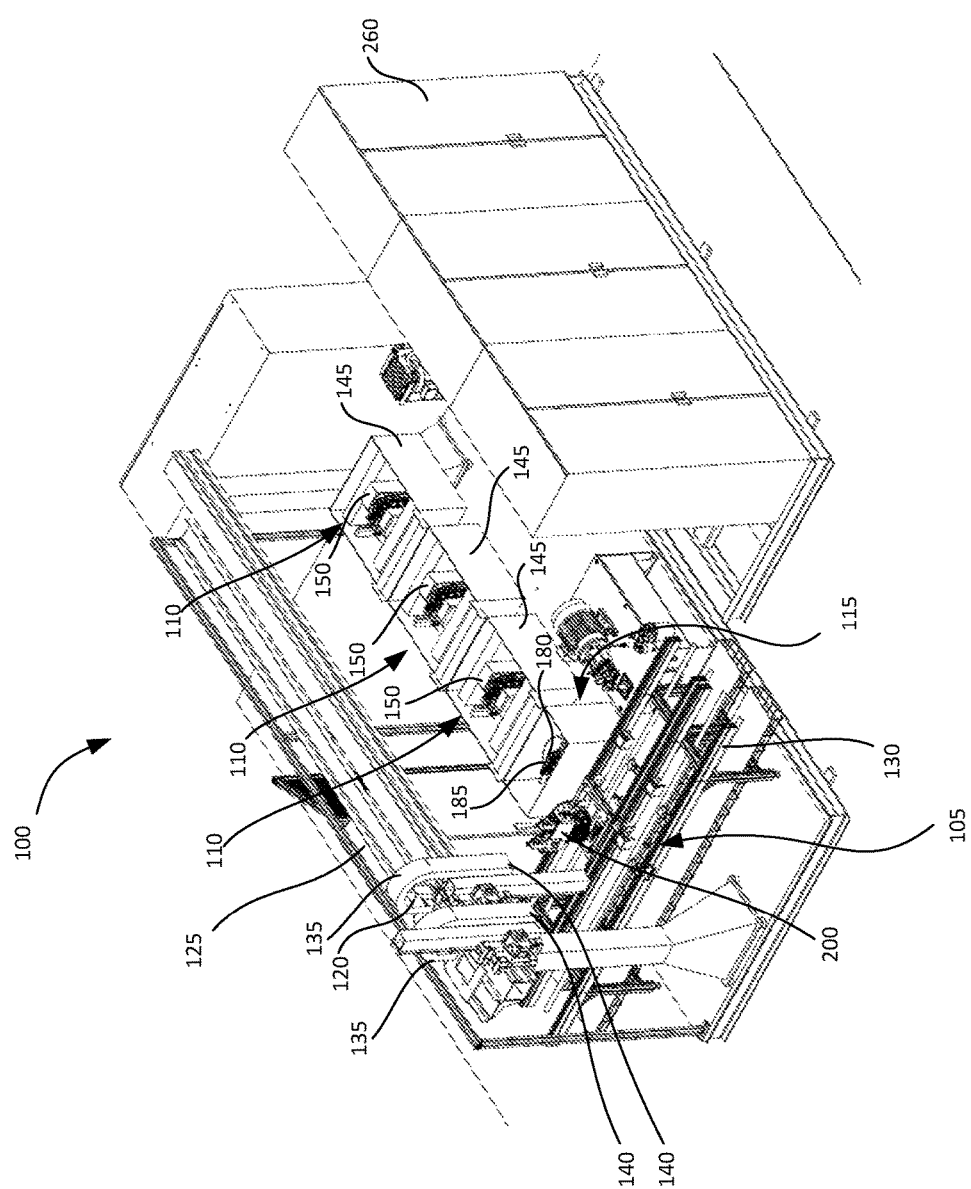
FIG. 1 illustrates a front right perspective view of an embodiment of a system for testing and calibration.
Figure 2:
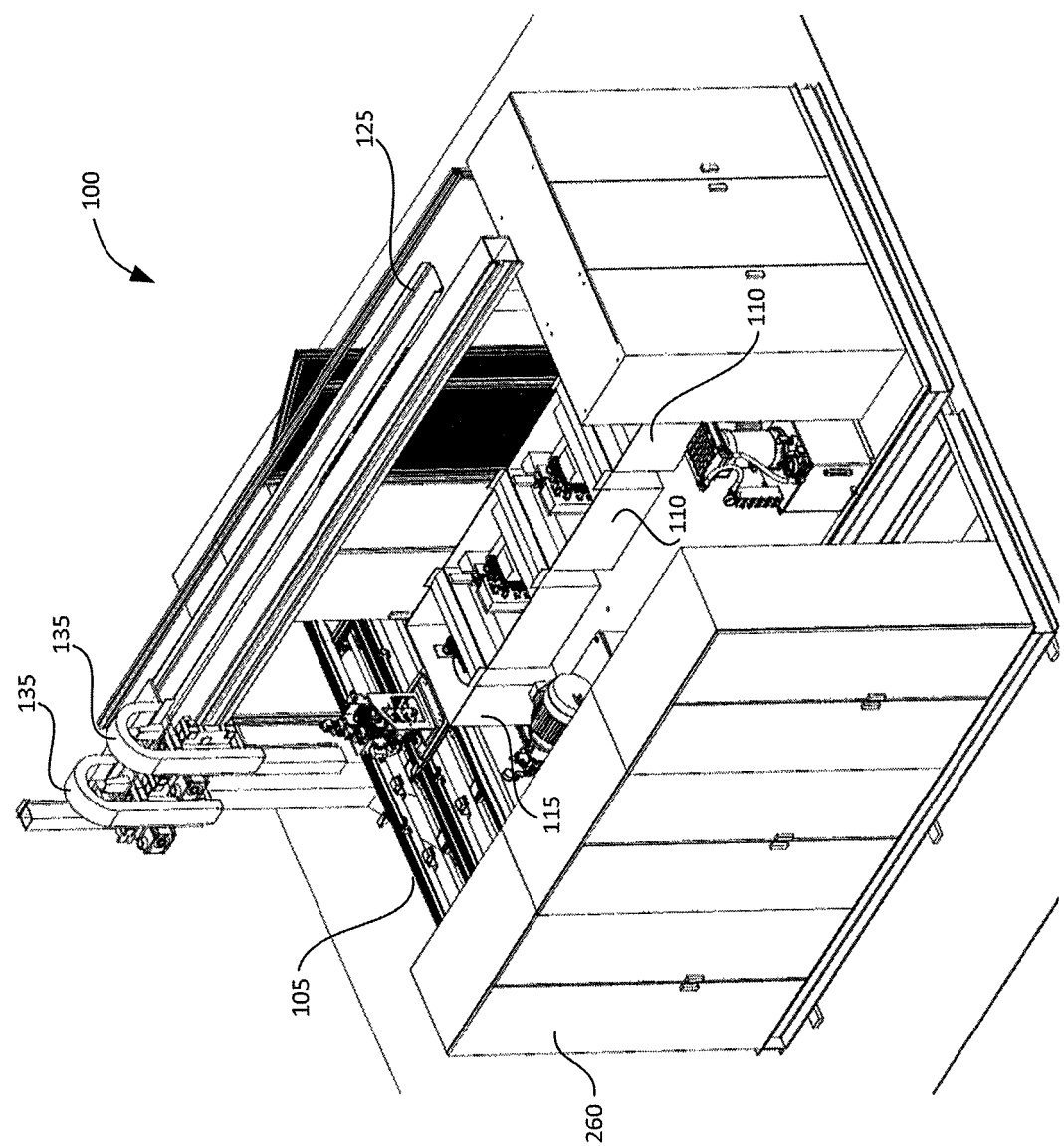
FIG. 2 illustrates a rear perspective view of the embodiment of the system in FIG. 1.

Generally the present disclosure relates to a system and method for testing in a pressurized and/or calibration in a pressurized and/or wet environment. In the following, the system and method are referred to as a system and method for testing but it will be understood that calibration may also be performed in appropriate embodiments/situations. Further, although the embodiments focus on a system and method for testing and calibration of a transmission control assembly, it will be appreciated that the principles and concepts disclosed can be used for testing and/or calibration of other parts, particularly parts that are tested or calibrated using the same or similar parameters as those in the embodiments shown and described herein.

The embodiments of the system and method described herein may allow for a more efficient, lower cost, lower floor space alternative to conventional systems and methods. In some embodiments, the cost reduction may be provided by replacing multiple conventional machines with one or two machines or systems that can operate on more parts at the same time. This may allow for a smaller number of duplicated sub-components and a more compact system.

Some embodiments of the system include a plurality of test stations configured to receive parts to be tested under pressure and, in some cases, in a wet environment under pressure. As noted above, the test stations may alternatively or also be calibration stations. In some cases, embodiments of the system include a cleaning station configured to clean the part after the part has been tested and/or calibrated in a wet environment and prior to loading the part on a conveyor or the like for further processing.

Further, some embodiments of the system and method for testing involve processing of a part in a generally vertical, upright orientation or position. Conventional systems typically process the part in a flat, horizontal or plane orientation or position because pressure clamping is typically performed using vertical presses. The use of a generally vertical orientation may enable a more compact footprint, an easier material handling robot, or fewer motions in the part handling and the test positions. This approach may provide lower costs and a compact machine. The vertical orientation may also allow the part to be put into the test clamp position somewhat like putting bread into a toaster and may reduce or eliminate extra motions, cycle time and the like that may be required in order to "lay flat" (i.e. make horizontal) a part inside a test clamp.

The system and method for testing may include a manifold with individual integrated piston clamp motions for the "test clamp". Conventional systems typically use a large press type mechanism. The use of individual piston motion may enable a compact test clamp mechanism, and less motion. This may result in a compact packaging of multiple "test clamps" and may enable multiple clamps (or test stations) in a single machine, having fewer motions to control, and reducing or eliminating the need for multiple machines with single or double controlled test clamps. The use of individual piston motion may also allows for quick change of fixtures and fixtures may be tested off-line for different parts.

The system and method for testing may also include the use of a cleaning mechanism, for example, a spin mechanism or the like. This may provide a method to remove post-test residual oil, or other testing fluid, from the part. Using a spin mechanism may allow for a compact foot-print such that this spinning process can be performed in-line by the same system as the testing, which may provide more efficient and compact handling.

FIGS. 1 to 4 illustrate an embodiment of a system for testing 100. The system includes a loading/unloading station 105, a plurality of test stations 110 (sometimes referred to as test fixtures or cells). In this embodiment, three test stations 110 are shown. The system 100 may optionally include a cleaning station 115. Parts 200 are moved among the test stations 100 and cleaning station 115 by a gantry robotic module 120 provided to a gantry 125 above the stations.

The loading/unloading station 105 is positioned to receive a conveyor 130 for moving parts 200 to and from the system 100. The gantry robotic module 120 provided to the gantry 125 moves a part 200 from the conveyor 130 to one of the plurality of test stations 110. As noted above, the test stations 110 may perform calibration processes as well as testing processes on the part 200. The embodiment shown in FIGS. 1 to 4 shows the gantry robotic module 120 with two moving mechanisms 135 and robotic grippers 140. In this way, the gantry robotic module 120 can more efficiently both load and unload the parts 200 from the test stations 110 as the gantry robotic module 120 moves along the gantry 125. For example, one moving mechanism 135 removes a part 200 while the other moving mechanism 135 places a part 200 in the test station 110.

Each test station 110 includes a container 145. The container 145 also contains a clamping mechanism 150, as illustrated in greater detail in FIG. 4 and also described further herein. In some embodiments, the container 145 may be configured to be filled with fluid, for example, oil.

Figure 4:
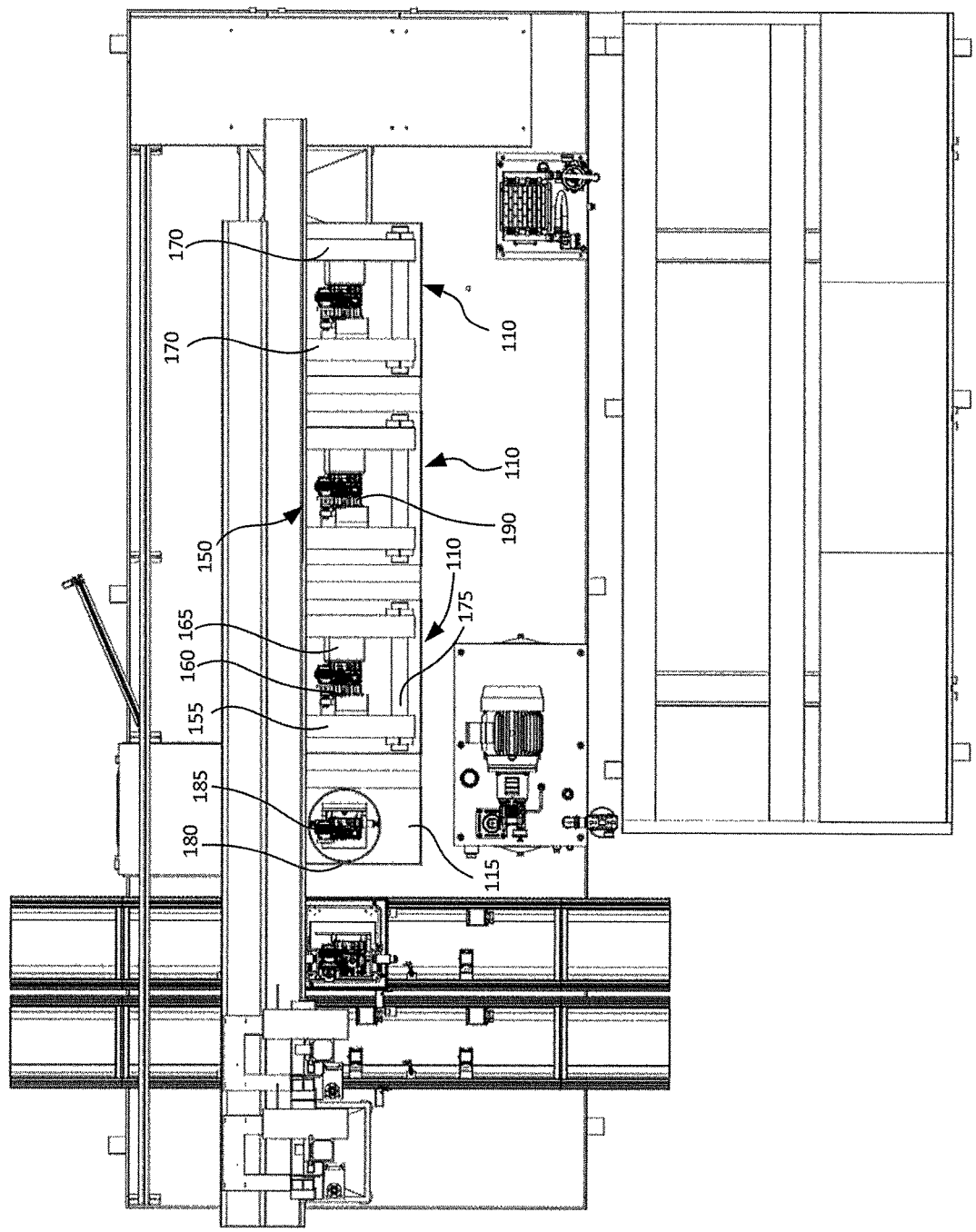
FIG. 4 illustrates a top view of the embodiment of the system in FIG. 1.

With reference to FIG. 4, the clamping mechanism 150 includes a clamp frame 155, a clamping module 160 (sometimes referred to as a manifold), and a seal manifold 165 (sometimes referred to as a base). The clamp frame includes two clamp plates 170 that are connected by a plurality of clamp bars 175. The clamp bars 175 securely hold the clamp plates 170 at a distance relative to each other with sufficient force to hold against the pressure generated in the test.

The clamping module 160 and seal manifold 165 are provided on the inner surfaces of the clamp plates 170, opposite from each. This can allow the part 200 to be positioned between the manifold 160 and the seal manifold 165. The clamping module 160 includes a plurality of hydraulic high pressure pistons 190. The pistons 190 can be activated to provide pressure and hold the part 200 in place against the seal manifold 165 for the test operation. In this particular embodiment, the plurality of pistons are configured to match with bolt locations on the part 200. The clamping module 160 and seal manifold 165 may be removably attached to the clamp plates 170. Removability may allow for ease of maintenance or changing of test operations. Further, in some embodiments, the clamp plates 170 may be incorporated into the container 145.

Each test station 110 is configured in a modular way so that test stations 110 can be added/removed from a system 100 depending on the part throughput required. In the embodiment of FIGS. 1 to 4, three test stations 110 are provided but, depending on the test or calibration requirements, the system 100 could be adapted for fewer or more test stations 110 and/or could be designed for a larger number than are actually in use initially to allow for larger volumes in the future.

When testing or calibrating in a wet environment, following a test/calibration operation, the part 200 may be coated with excess liquid, for example, oil. In this case, the part 200 can be moved by the gantry robotic module 120 to the cleaning station 115 to remove excess liquid. The cleaning station 115 includes a container 180 and, in this embodiment, a spinning mechanism 185 in the container 180. The container 180 may include a lid (not shown) that can be closed during operation. The spinning mechanism 185 is configured to receive and hold the part 200 following test/calibration. The spinning mechanism 185 rotates at an appropriate rate for an appropriate time to remove excess oil that remains on the part 200 following test/calibration. The use of a cleaning station 115 may help to reduce oil dripping from the part 200 following the test/calibration. In some embodiments, the part 200 may have some residue after being cleaned (e.g. depending on the subsequent processing). As with the test station 110, the cleaning station 115 may be designed in a modular fashion. This may help with maintenance and interchangeability with cleaning stations in other systems. In some embodiments, other methods of removing/reducing excess liquid may be used depending on the application, including, for example, air drying, shaking, or the like.

Following either testing, calibration or cleaning (as appropriate), the part 200 is moved by the robotic module 120 from the cleaning station 115 to the conveyor 130, where the part will be advanced for separate processing.

Figure 3:
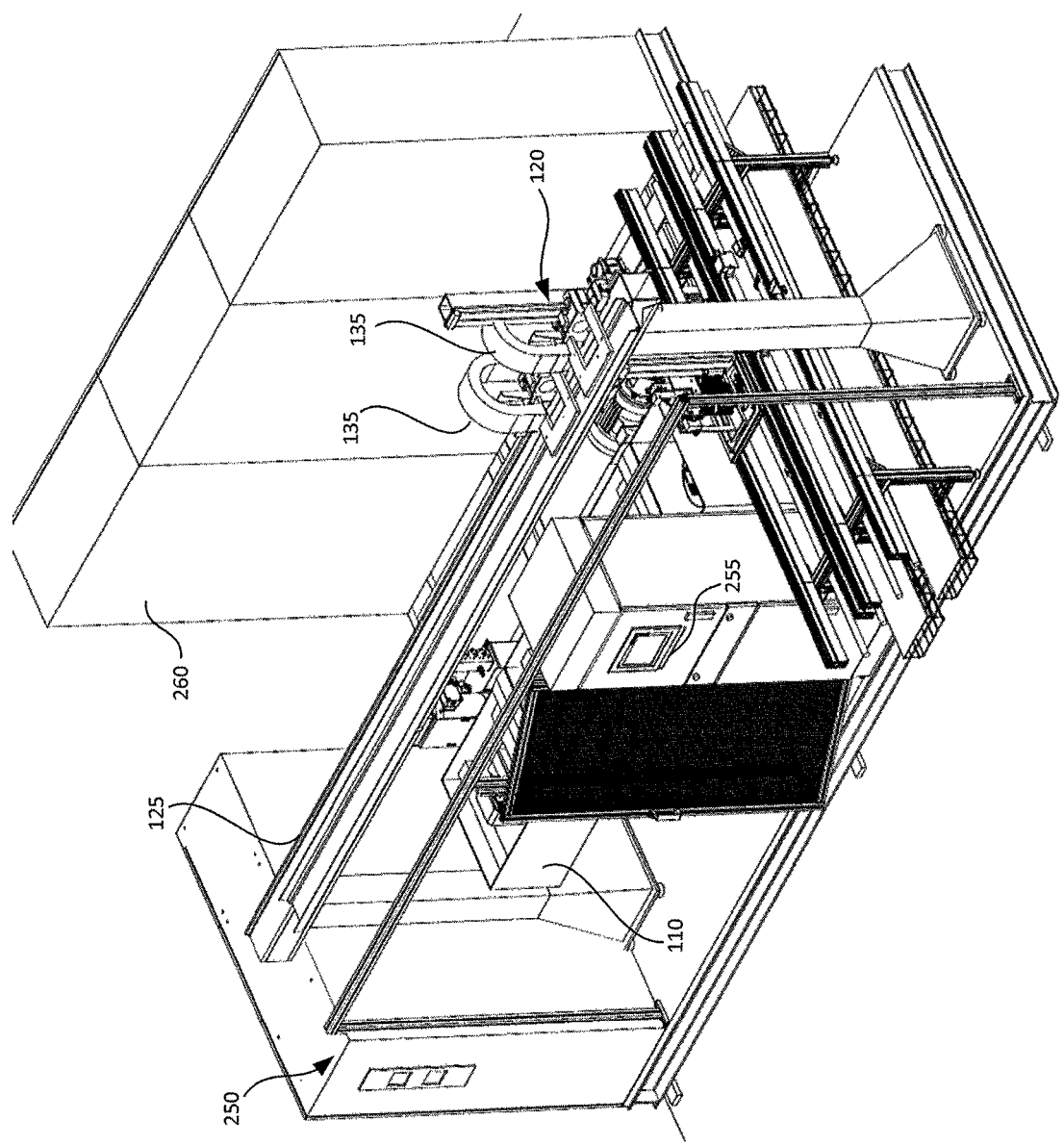
FIG. 3 illustrates a front left perspective view of the embodiment of the system in FIG. 1.

FIG. 3 illustrates a power station 250, for example an electronic control panel configured to provide power to the test stations 110 and the cleaning station 115, and a control station 255, for example a data acquisition panel, for the system 100. FIG. 3 further illustrates test panels 260, which house test circuits for each of the test stations 110. The test panels are at the side of the system 100 and may be at some distance from the actual test stations 110. When a test station 110 requires a change or a repair, the test station 110 may be removed from the system. To remove the test station 110, lines (not shown but may include electrical and hydraulic connections or the like) connecting the test station 110 and the test panels 260 will generally need to be disconnected, which may take additional time and effort. Further, the new or repaired test station 110 will not be able to be operated until it is reconnected to the test panel 260.

Figure 5:
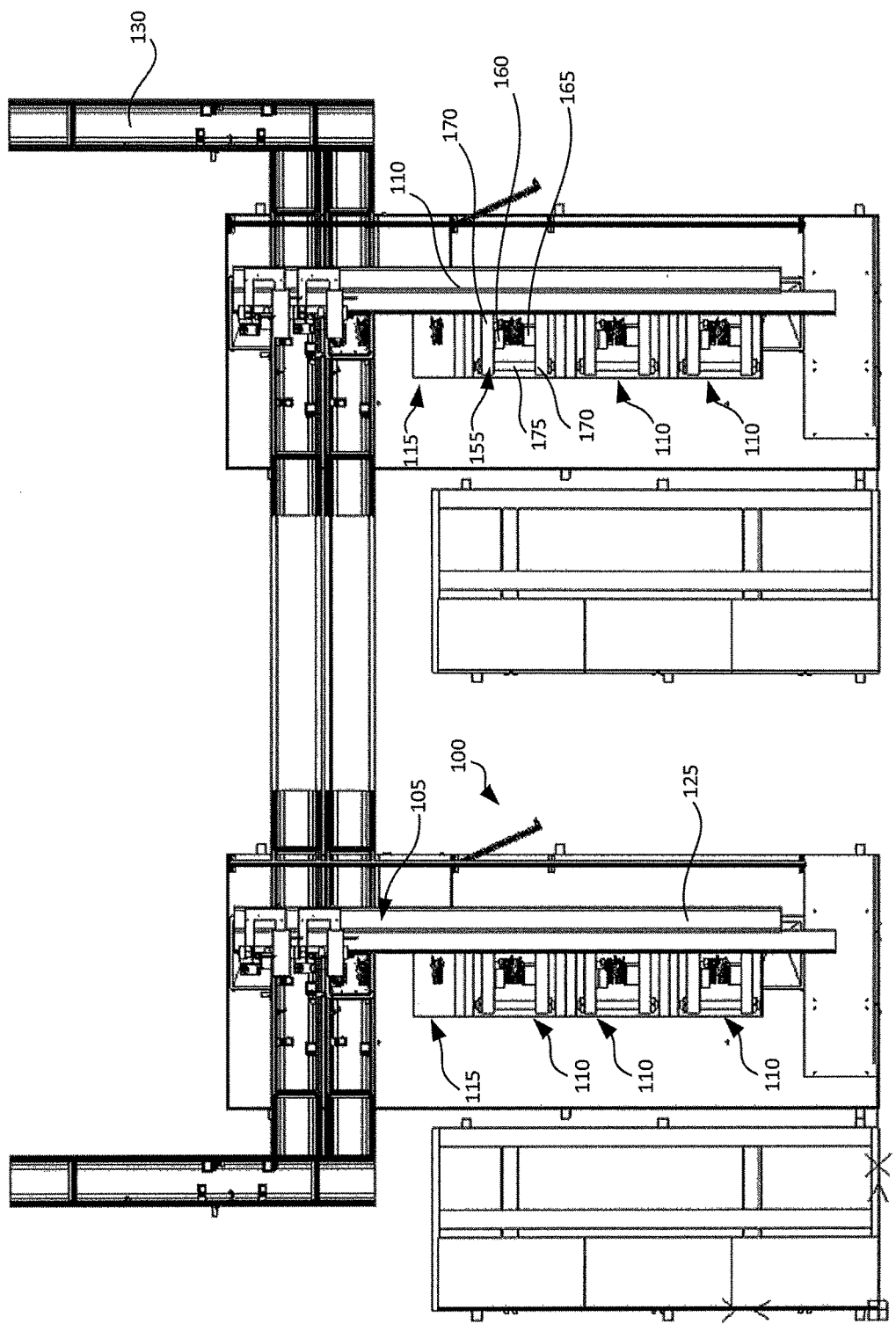
FIG. 5 illustrates a top view of an embodiment having a plurality of systems similar to those illustrated in FIG. 1.
Figure 6:
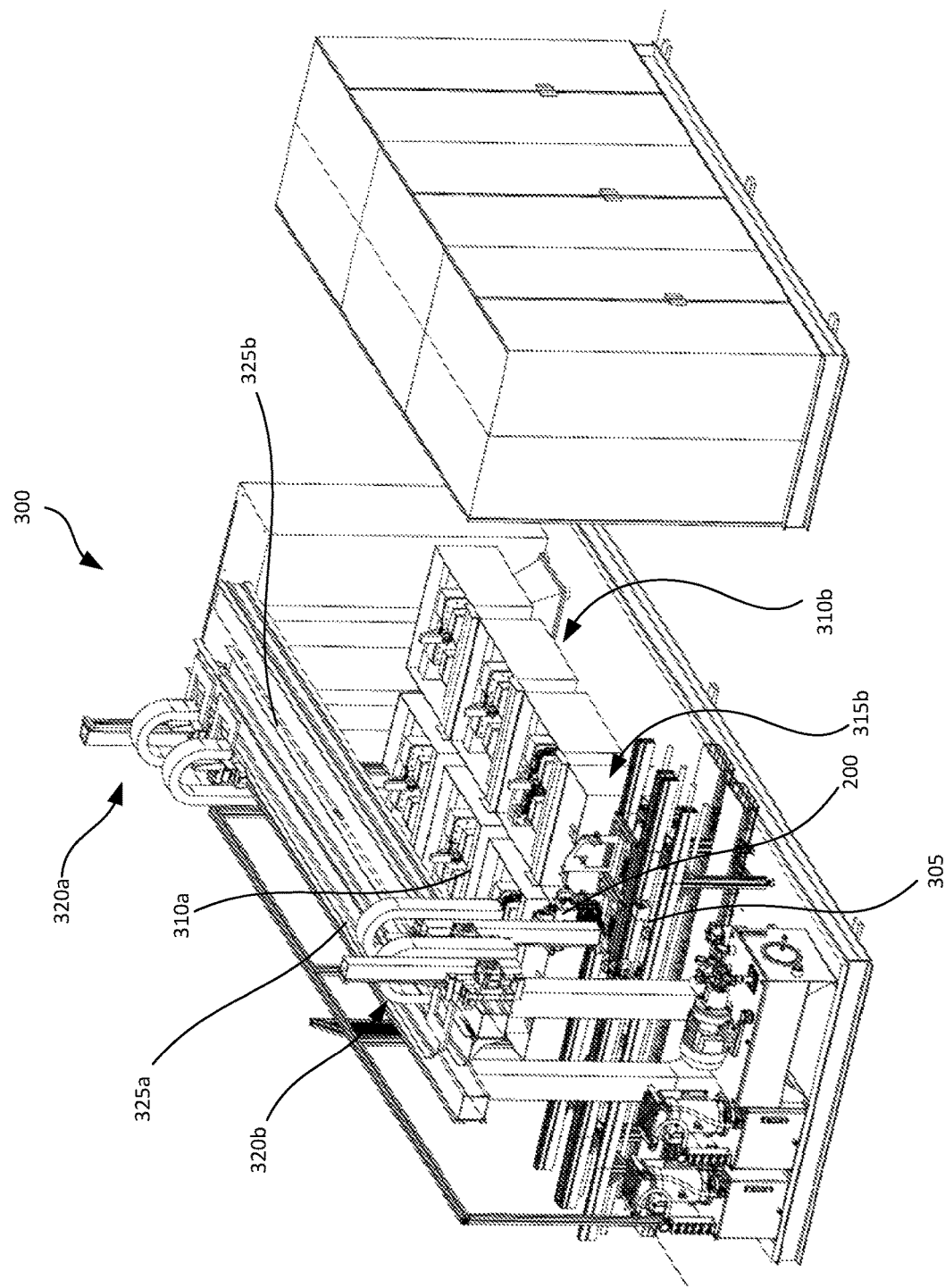
FIG. 6 illustrates a front right perspective view of another embodiment of the system for testing and calibration.
Figure 7:
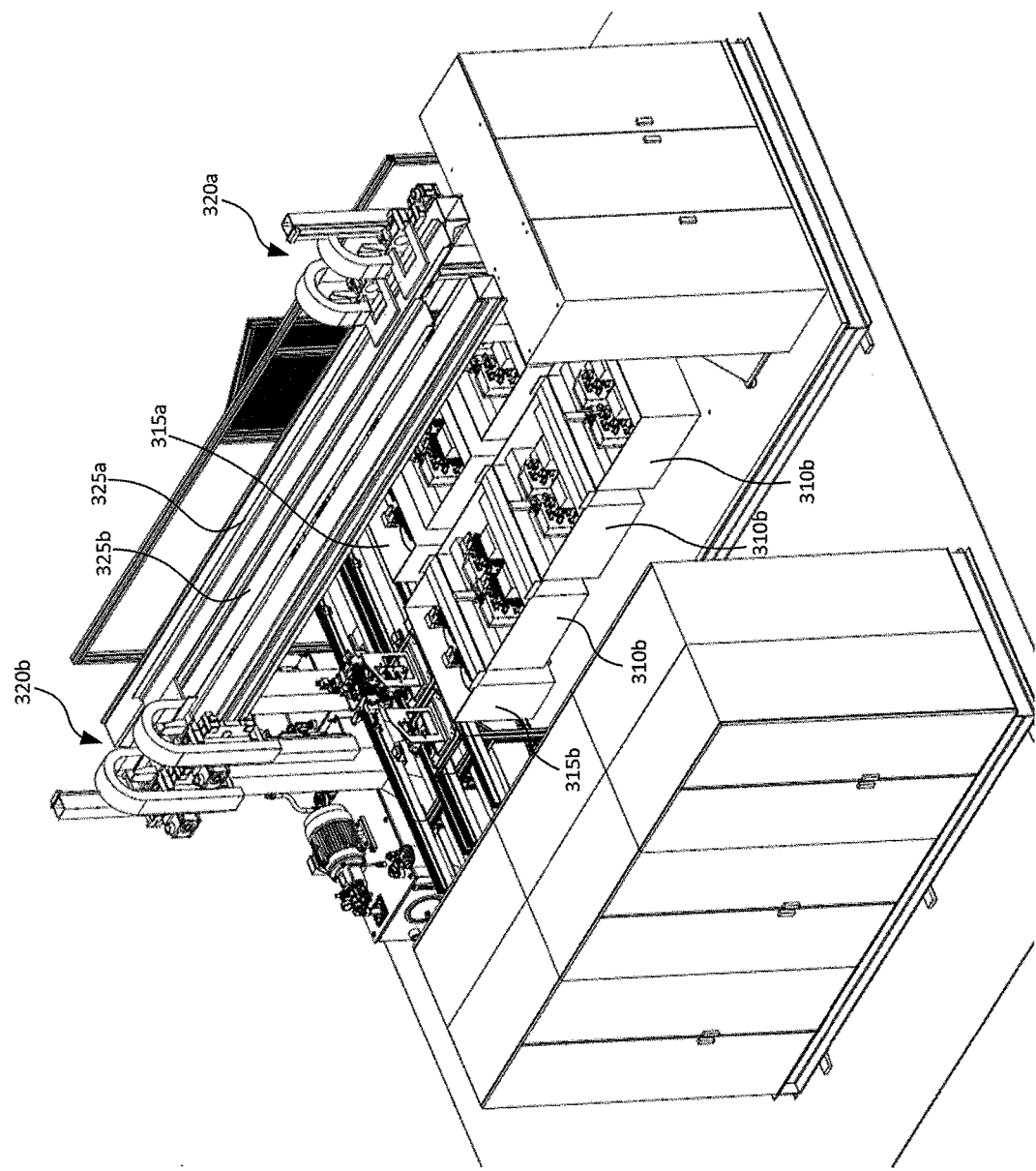
FIG. 7 illustrates a rear perspective view of the embodiment of the system in FIG. 6.
Figure 8:
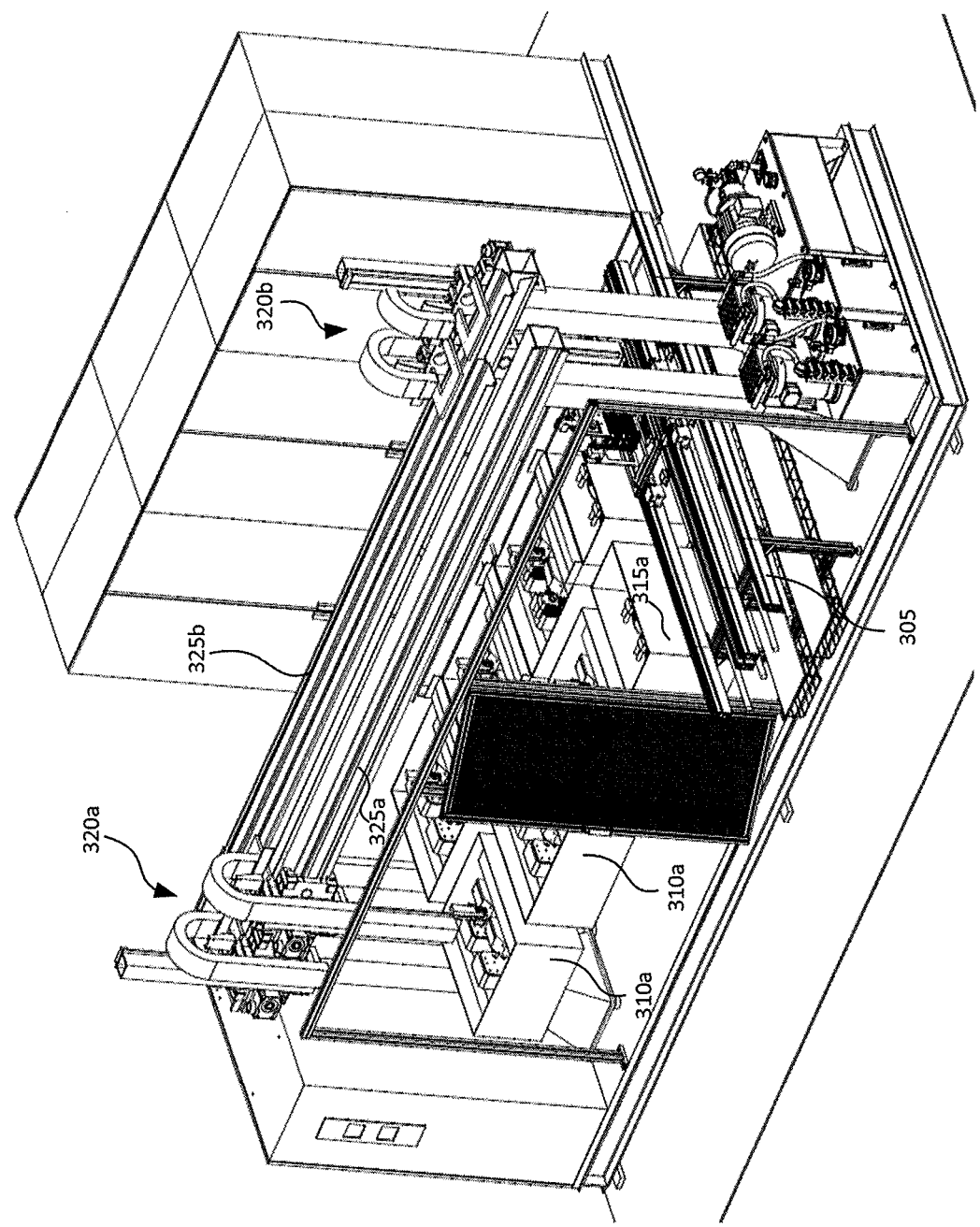
FIG. 8 illustrates a front left perspective view of the embodiment of the system in FIG. 6.
Figure 9:
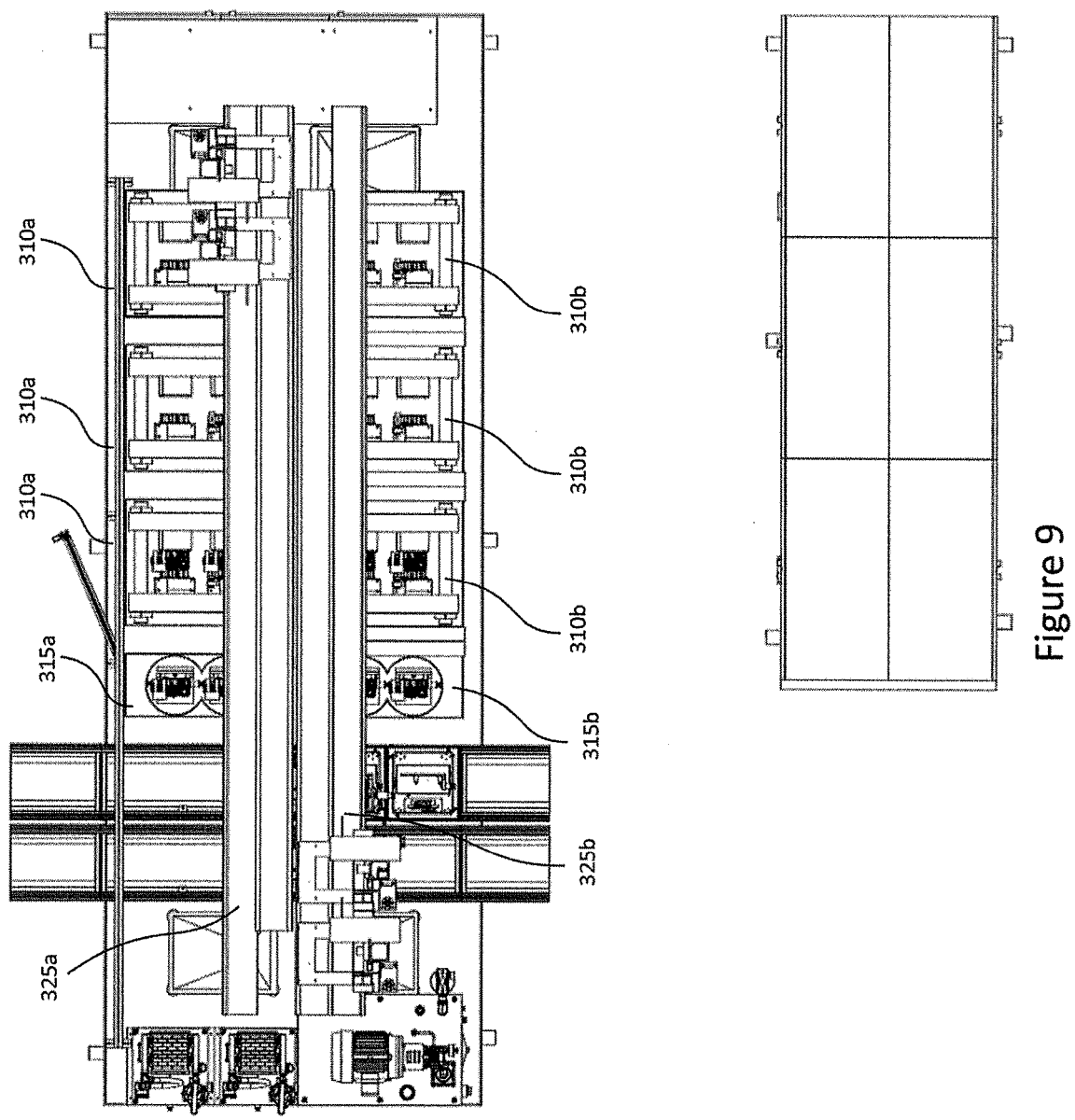
FIG. 9 illustrates a top view of the embodiment of the system in FIG. 6.

As shown in FIG. 5, a plurality of the systems 100 may be operated in parallel. In some embodiments, the plurality of systems may use the same conveyors 130 for providing parts to the systems.

Figure 10:
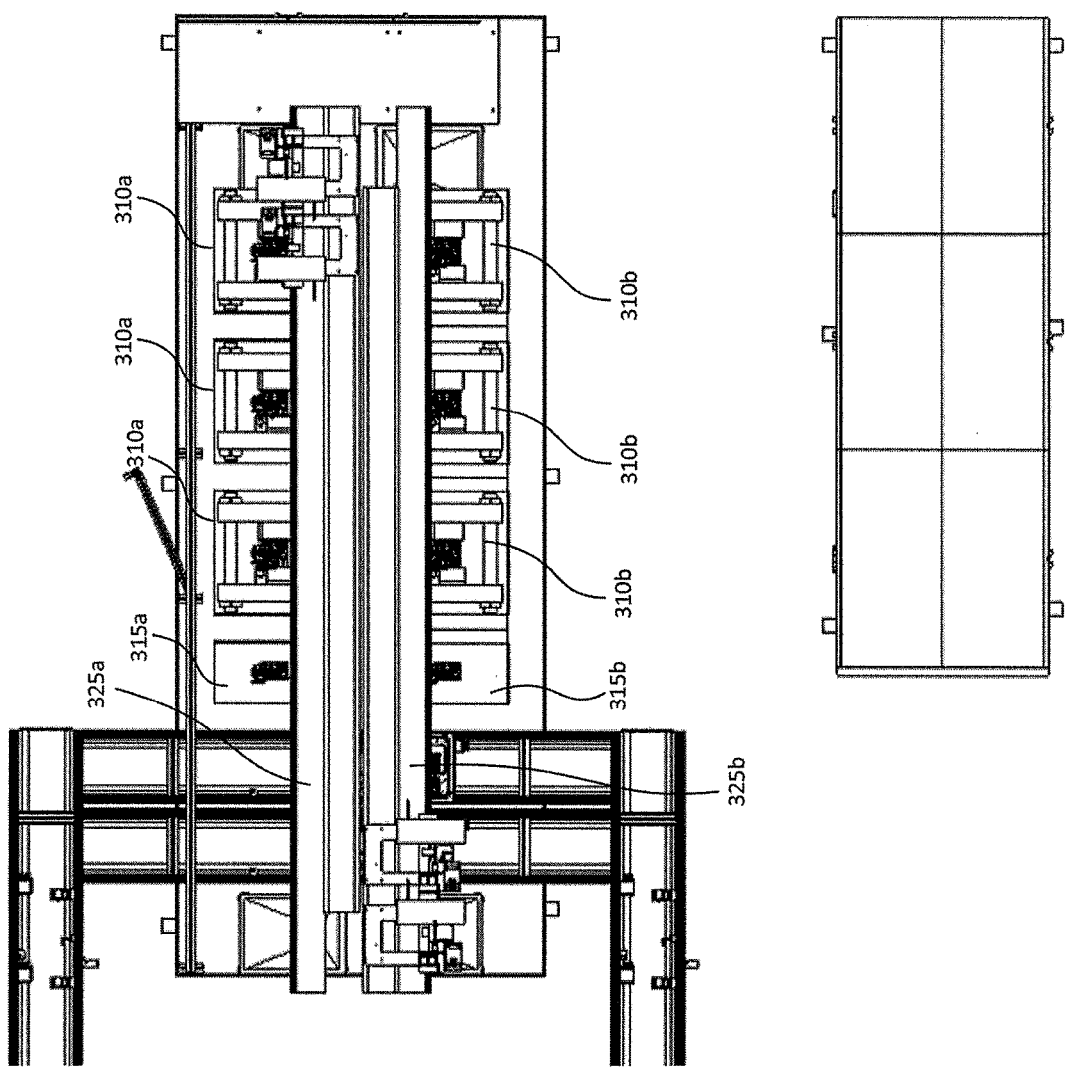
FIG. 10 illustrates a top view of a variation of the embodiment of the system in FIG. 6.

FIGS. 6 to 9 illustrate another embodiment of a system 300 for testing and calibration. The system 300 may include a load and unload station 305 configured to receive parts 200 from a conveyor 330. The system 300 includes a first and a second gantry 325*a* and 325*b* and a first and second row of test stations 310*a* and 310*b*. The first and second gantry 325*a* and 325*b* are placed in-line with the test stations 310*a* and 310*b*. Generally speaking, there may also be a first and second cleaning station 315*a* and 315*b* provided as well. Although not shown, embodiments of the system such as shown in FIGS. 6 to 10 may also be arranged with other similar systems and having appropriate feeder conveyors to allow greater throughput of parts. In some cases, the first gantry 325*a* may take parts from a first lane of the conveyor 130 and the second gantry 325*b* may take parts from the second lane of the conveyor 130. Overall, the system 300 of FIGS. 6 to 9 is similar to the system 100 of FIGS. 1 to 4 but with two lanes of test stations 310*a* and 310*b*. FIG. 10 illustrates a variation of the system 300 of FIGS. 6 to 9 with an alternate feeding mechanism.

Figure 11:
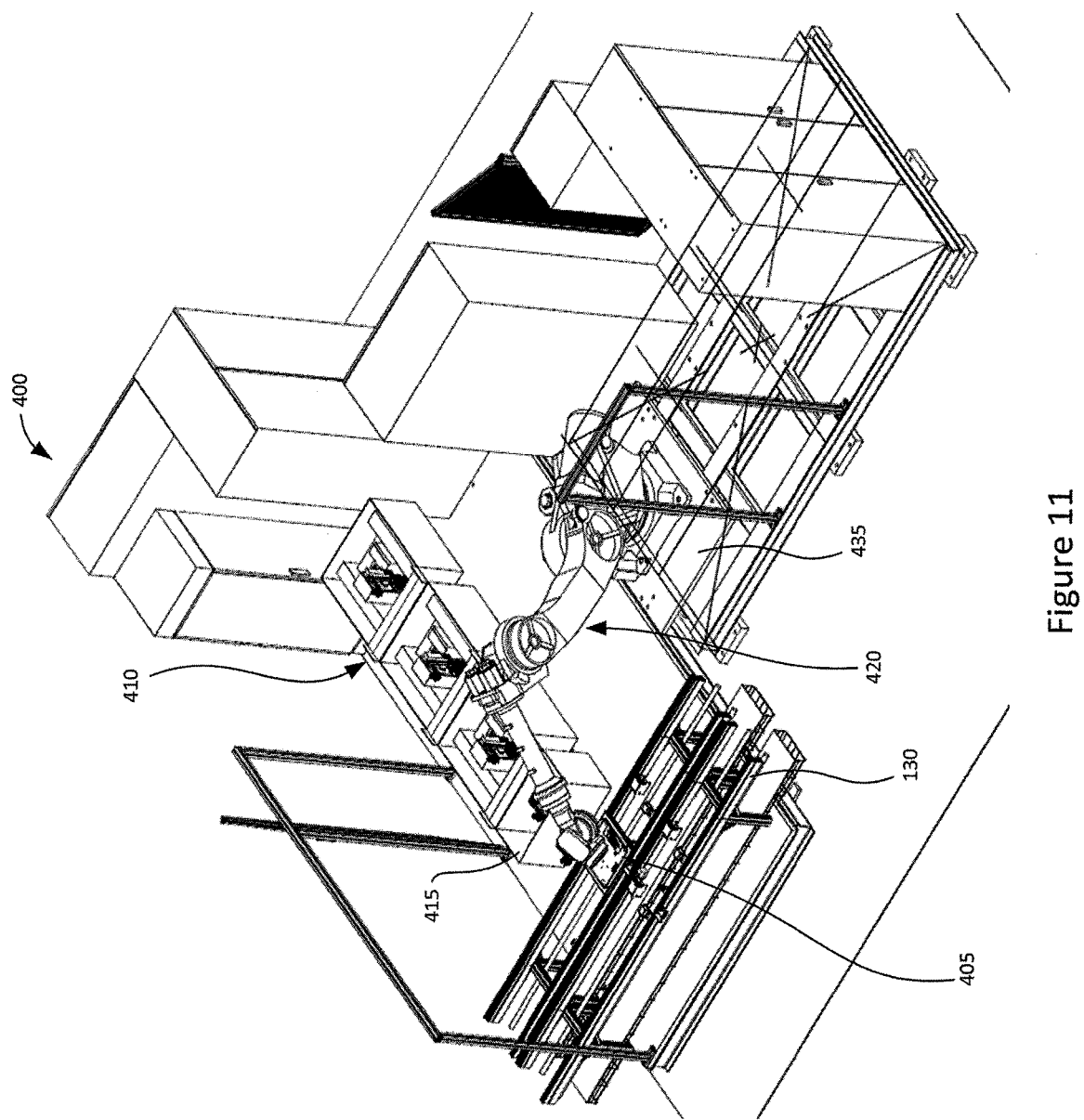
FIG. 11 illustrates a front right perspective view of yet another embodiment of a system for testing and calibration.
Figure 12:
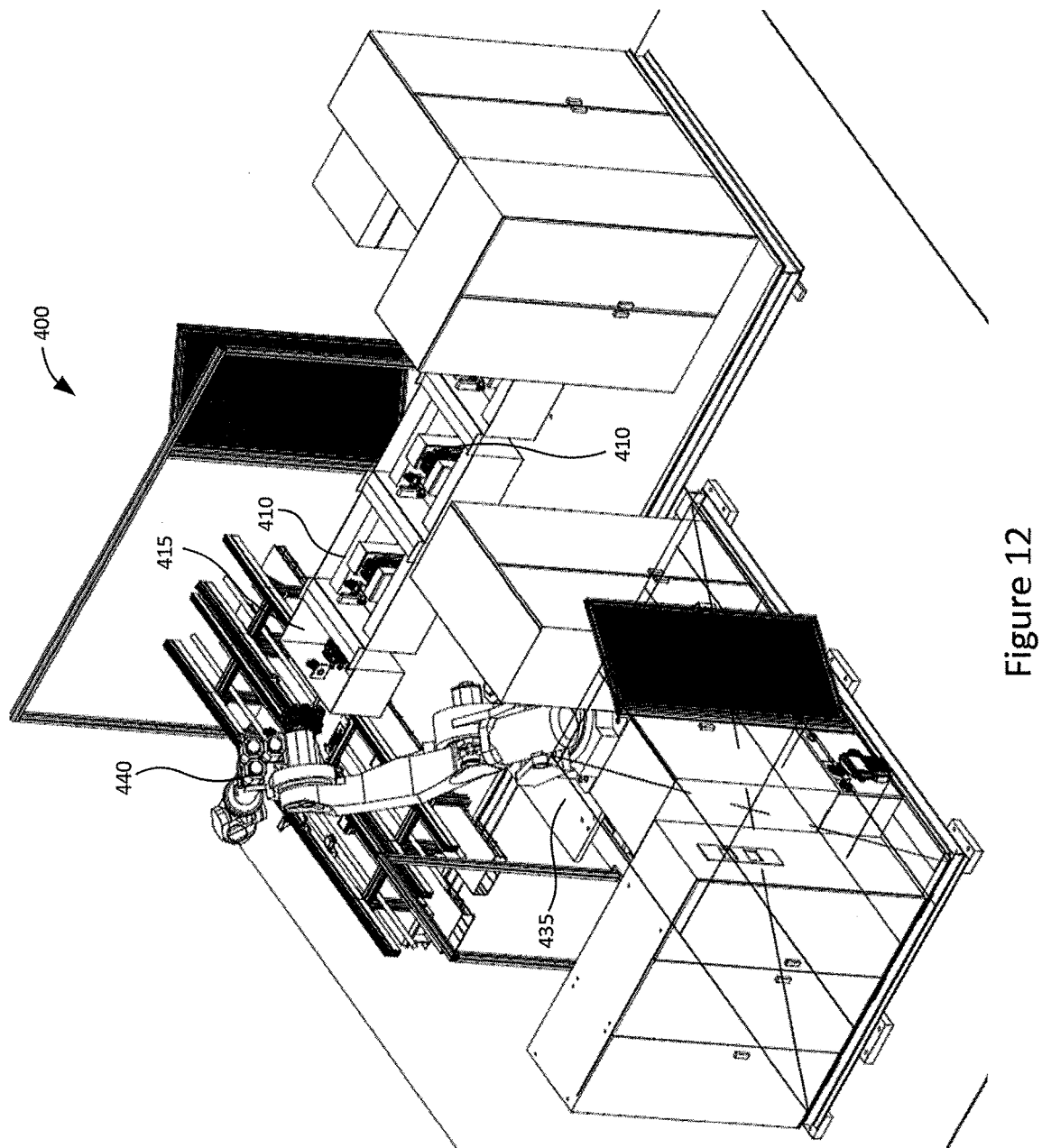
FIG. 12 illustrates a rear perspective view of the embodiment of the system in FIG. 11.
Figure 13:
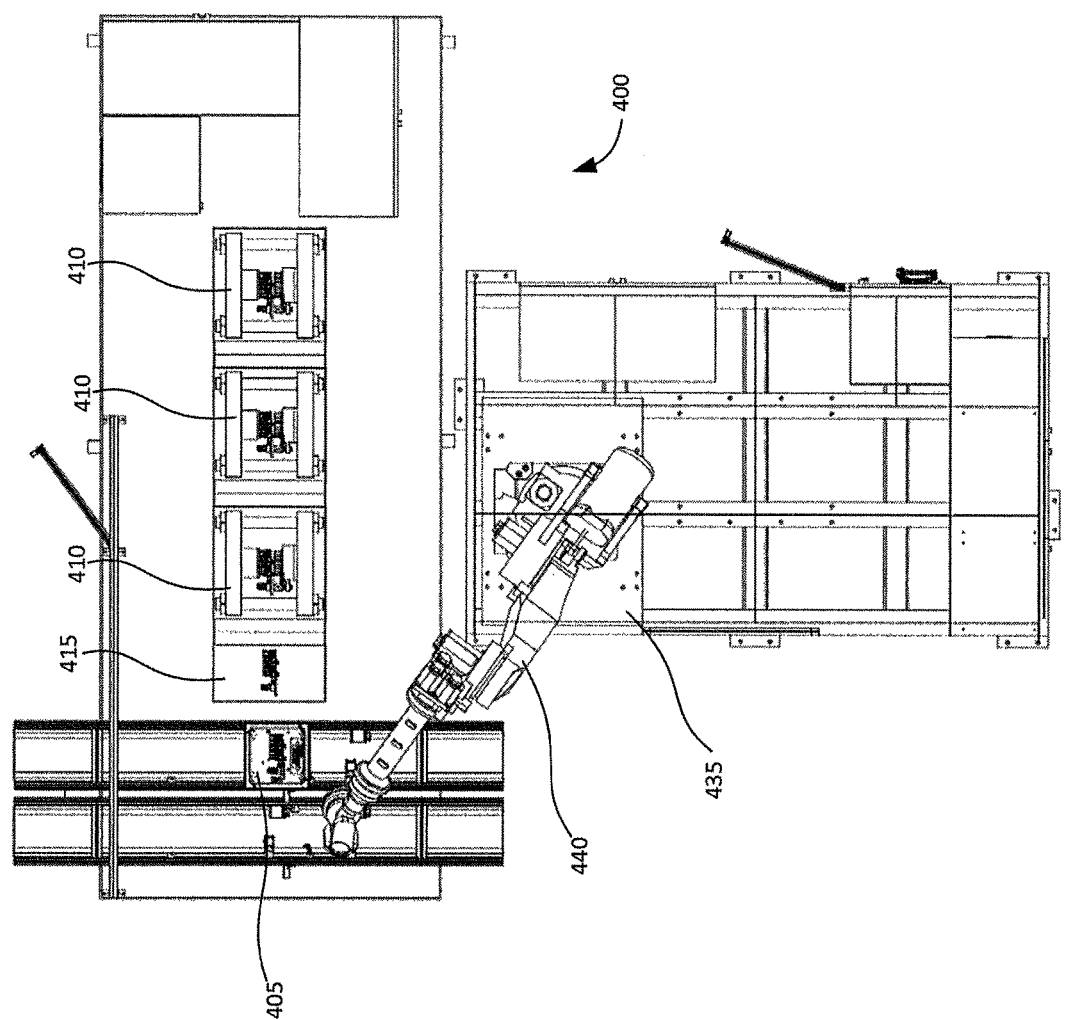
FIG. 13 illustrates a top view of the embodiment of the system in FIG. 11.

FIGS. 11 to 13 illustrate still another embodiment of a system 400 for testing. This embodiment provides for the movement of the parts 200 in the system 400 to be performed by a robotic module 420 that includes a floor mount 435 and a robotic arm 440, rather than a gantry, moving mechanism and gripper, to move the parts among a load/unload station 405, at least one test station 410, and at least one cleaning station 415.

Figure 14:
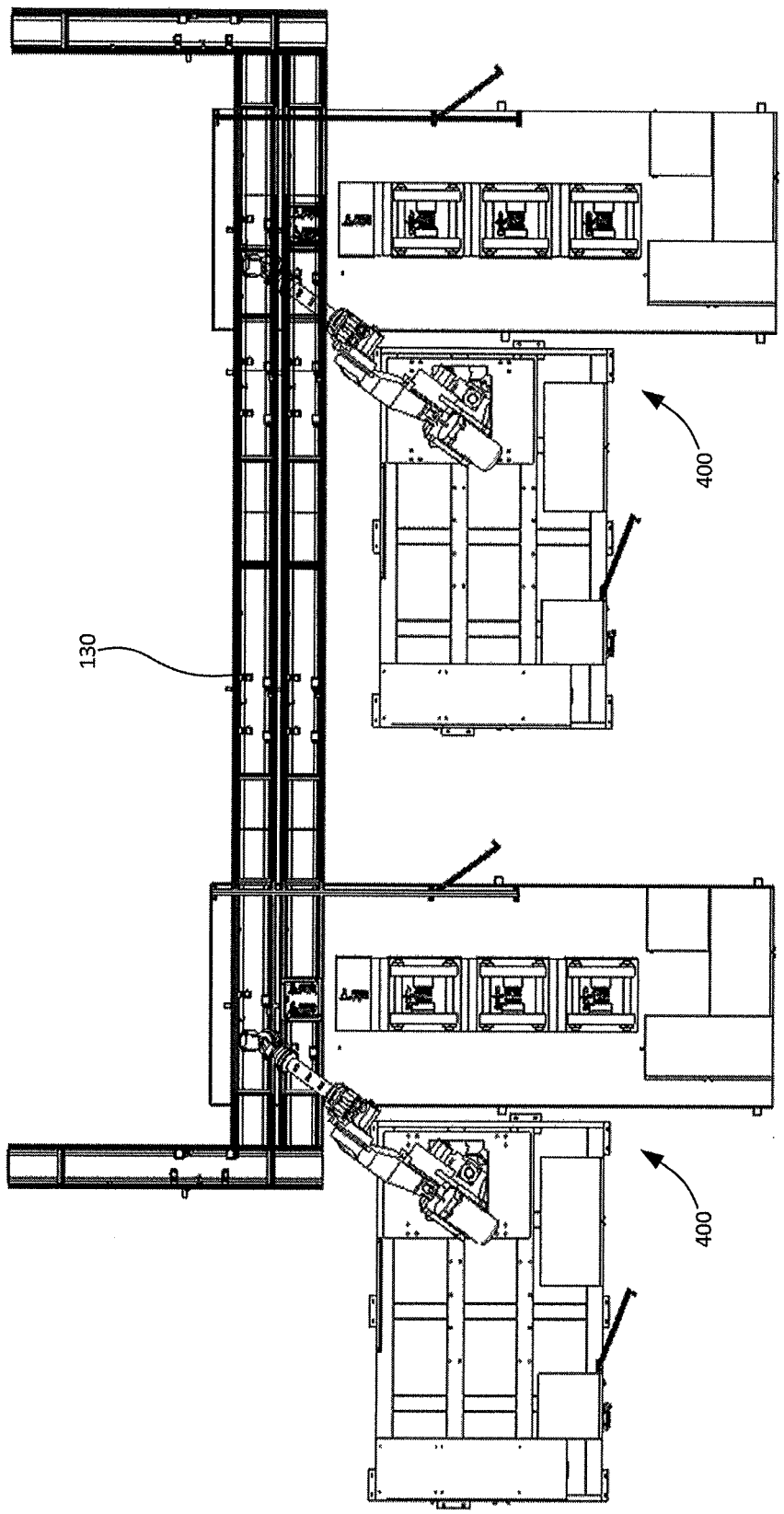
FIG. 14 illustrates a top view of an embodiment having a plurality of systems similar to those in FIG. 11.

FIG. 14 illustrates a top view of an embodiment having a plurality of systems similar to those in FIG. 11 operating in parallel.

Figure 15:
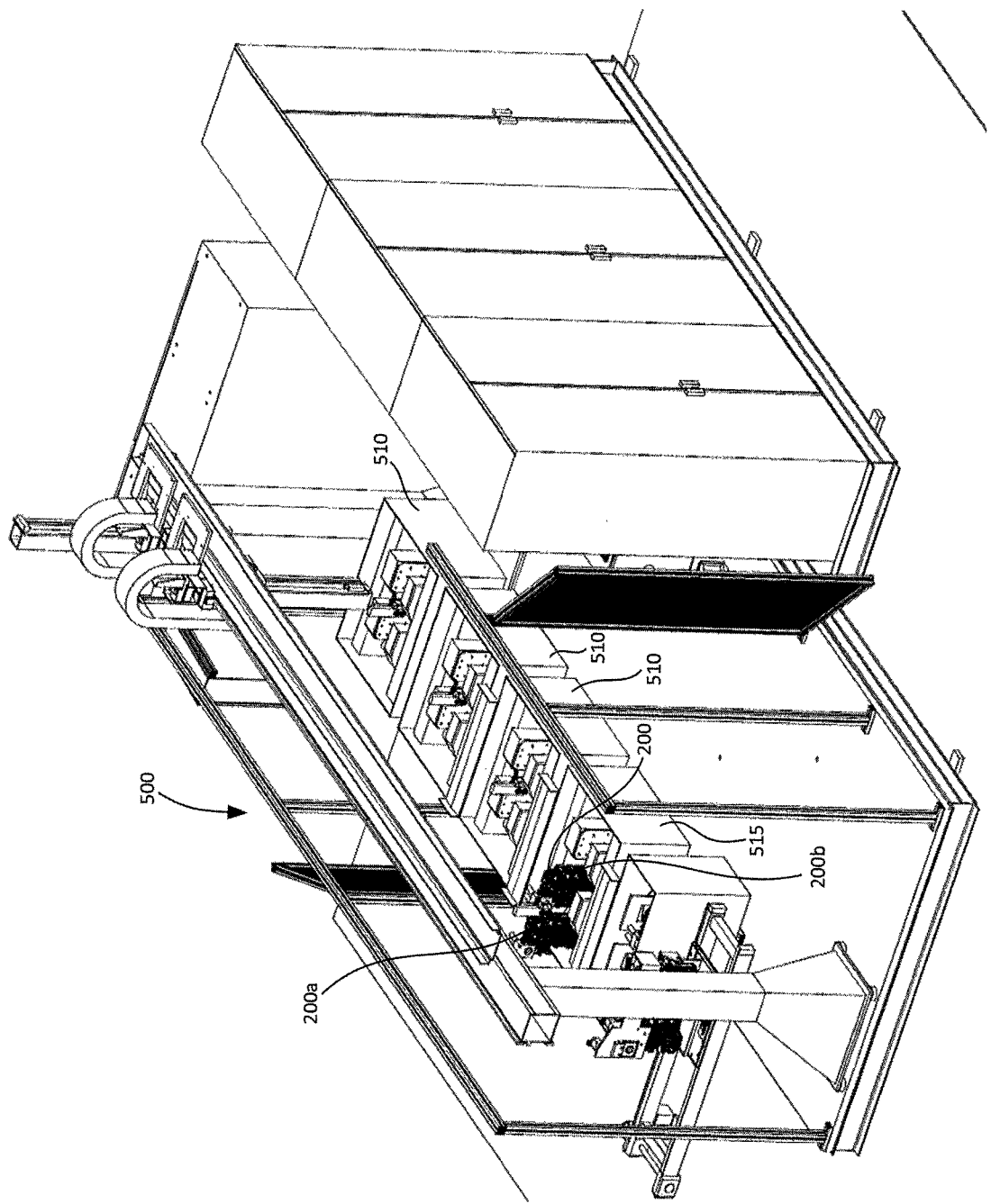
FIG. 15 illustrates still another embodiment of a system for testing and calibration in which the system is configured to work on two parts simultaneously.

FIG. 15 illustrates an embodiment of a system 500 for testing that is somewhat similar to that of the system 100 of FIGS. 1 to 4. One difference is that the system 500 has been modified such that each test station 510 can contain multiple parts 200, in this case, two parts, for example a part "A" 200A and a part "B" 200B, at the same time. This may allow for either simultaneous testing or for alternating testing or the like. In this embodiment, depending on the configuration, the test station 510 may be loaded with either different types of parts (in order to allow flexibility in manufacturing operations) or the same type of parts (for higher throughput of the same type of part). It will be understood that it may be useful to also modify a cleaning station 515 to be able to handle multiple parts in a similar manner.

Figure 16:
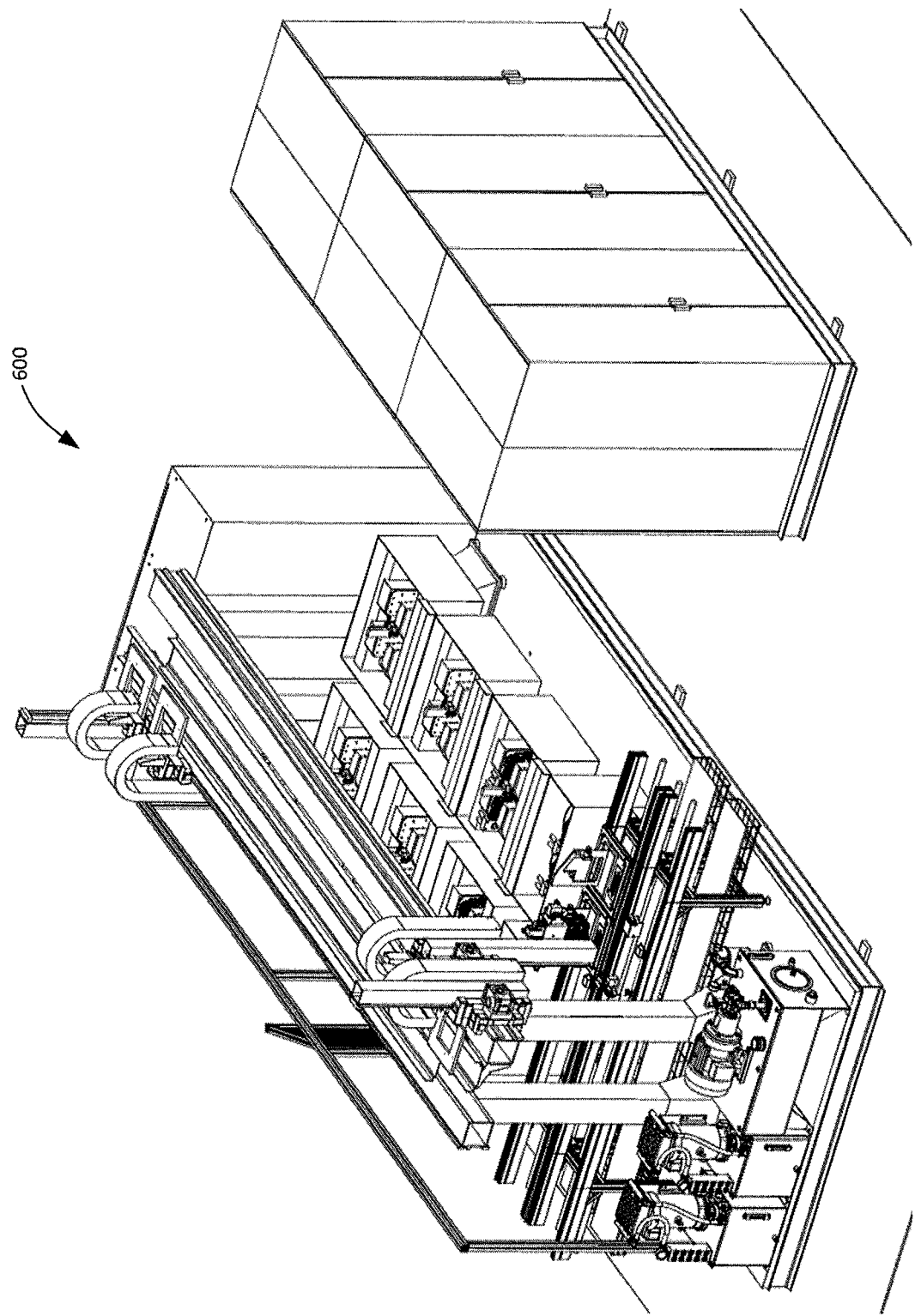
FIG. 16 illustrates still yet another embodiment of a system that is similarly configured to that of FIG. 15.

FIG. 16 illustrates another embodiment of a system 600 with a similar modification to that of FIG. 15 but based on the system 300 of FIGS. 6 to 9.

Figure 17:
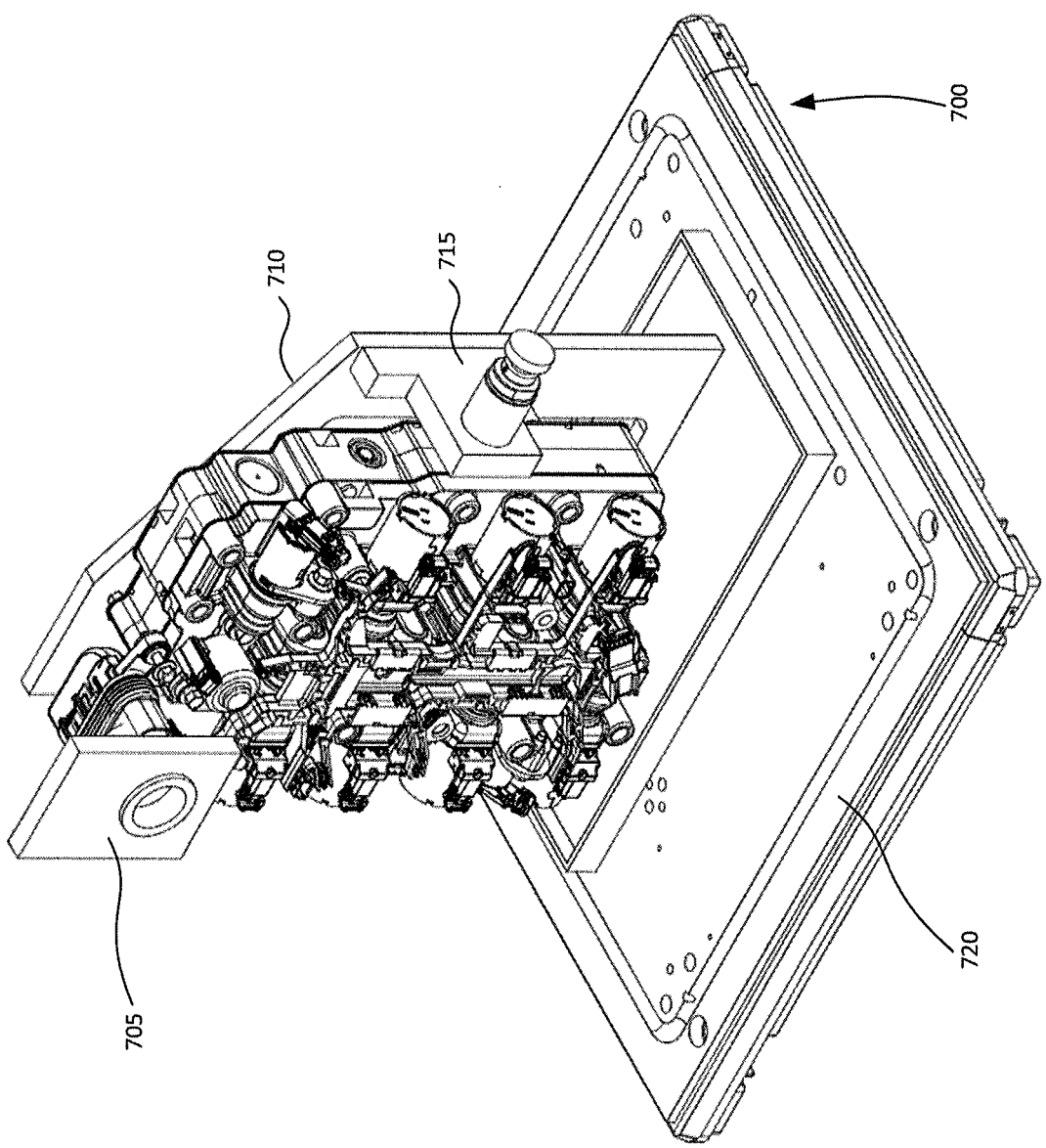
FIG. 17 illustrates a pallet according to an embodiment herein for carrying a part for loading into the system.

FIG. 17 illustrates an embodiment of a pallet system 700 for carrying a part for loading into an embodiment of a system, such as that of FIG. 1. In particular, the part 200 is loaded having a vertical orientation or upright position. The pallet system 700 includes an adapter 705 to be connected during the test/calibration. The adapter 705 may be picked up with the part 200 by the robotic module. A fixture 710 on the pallet 700 includes a lock/release mechanism 715 that allows the robotic gripper to grip the part and maintain its orientation during gripping and movement. In some cases, the lock/release mechanism 715 may be a hook mechanism configured to allow the robotic gripper to connect to and lock with the hook. In other cases, the lock/release mechanism 715 may be configured to provide for a magnetic lock, or a friction fit with the robotic gripper. In still other cases, the lock/release mechanism may have retractable pins configured to engage the robotic gripper. The base 720 of the pallet system 700 may remain on the conveyor 130 during processing of the part 200.

Figure 18B:
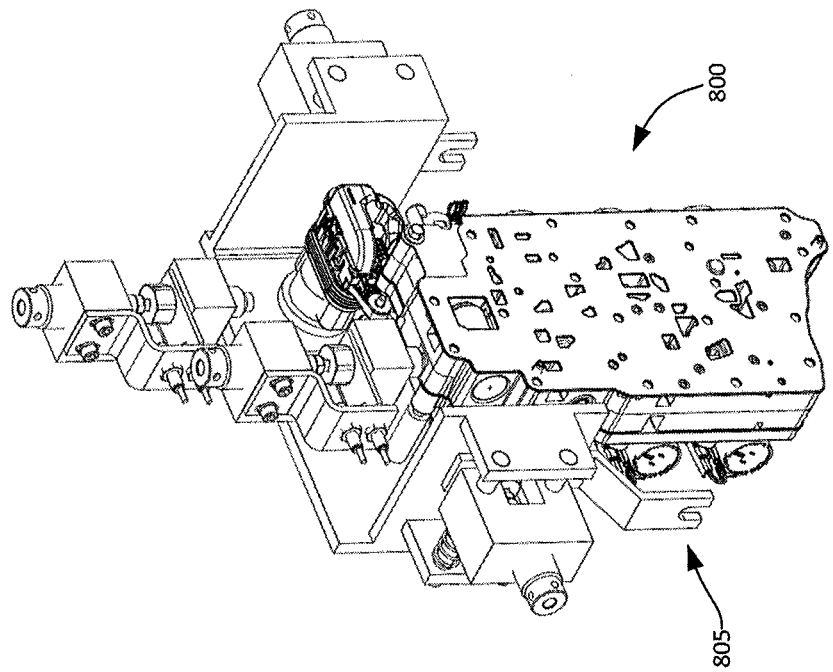
FIGS. 18A and 18B illustrate a gripper according to an embodiment of the system for testing/calibration.
Figure 18A:
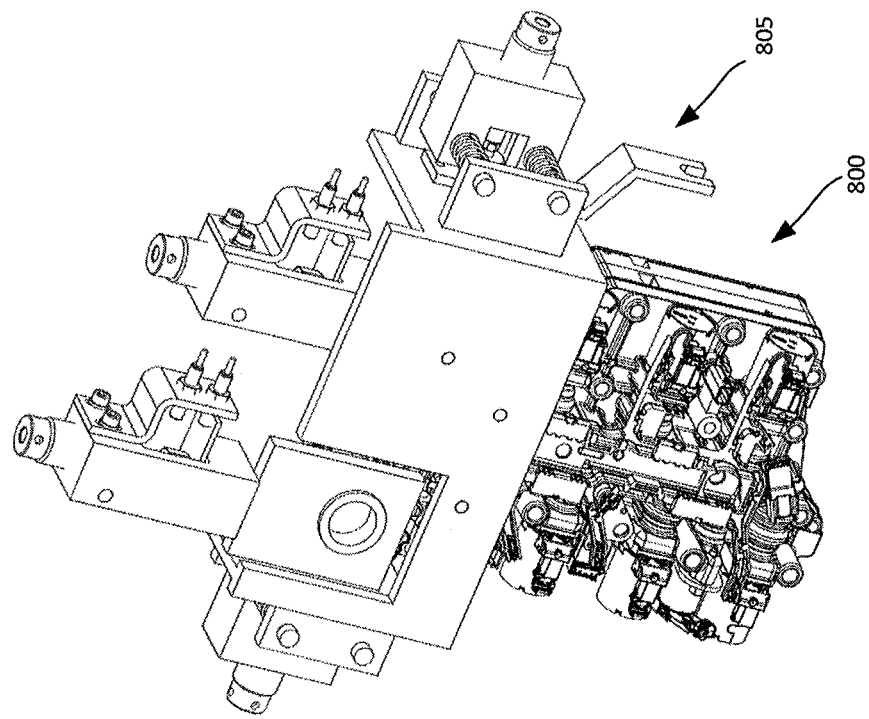

FIGS. 18A and 18B illustrate an embodiment of a gripper 800 for gripping the part 200 and moving the part 200 among the stations in the system. The gripper 800 is configured to maintain the orientation of the part 200 and adapter 705 during movement and is also provided with a gripper lock/release mechanism 805 that interacts with the pallet lock/release mechanism 715 such that control of the part 200 is maintained. In some cases, the gripper lock/release mechanism 805 may be configured to lock to a hook, or may include a magnetic lock or friction fit in order to engage the lock/release mechanism 715. In other cases, the gripper lock/release mechanism 805 may include retractable pins configured to engage the lock/release mechanism 715. In this manner, the gripper 800 may take the part to be tested into the test station and the pallet may remain on the conveyor 130.

Figure 19:
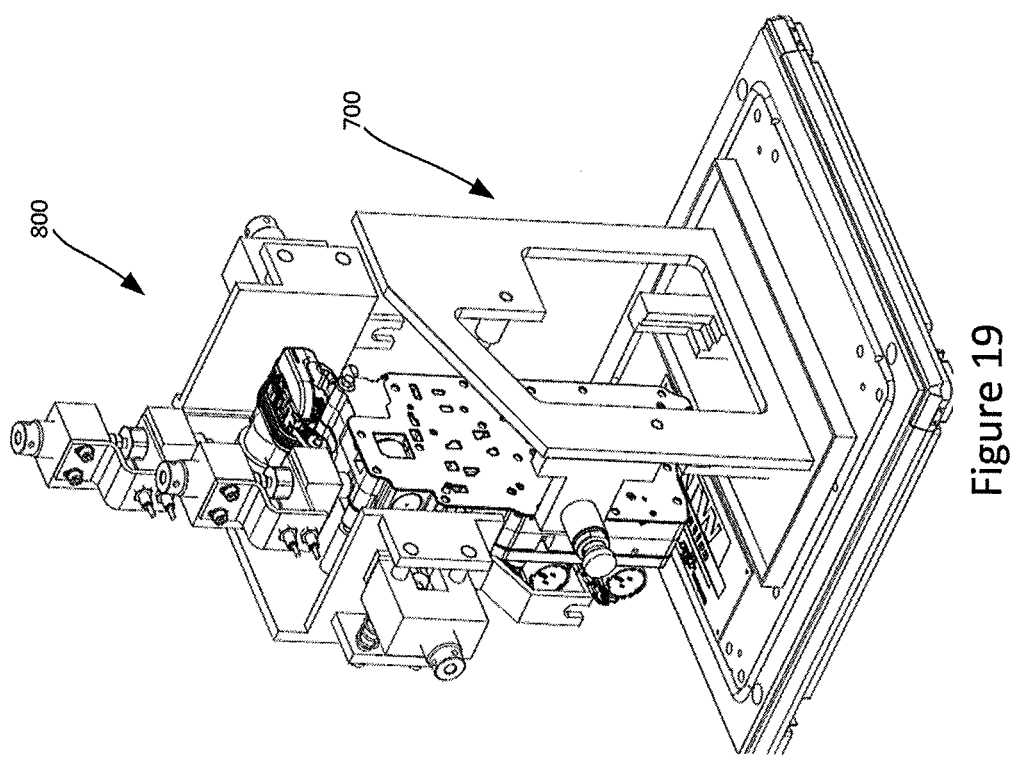
FIG. 19 illustrates the interaction of the gripper and the pallet while loading/unloading a part.

FIG. 19 illustrates the interaction of the gripper 800 and the pallet 700 while loading/unloading the part 200.

Figure 20:
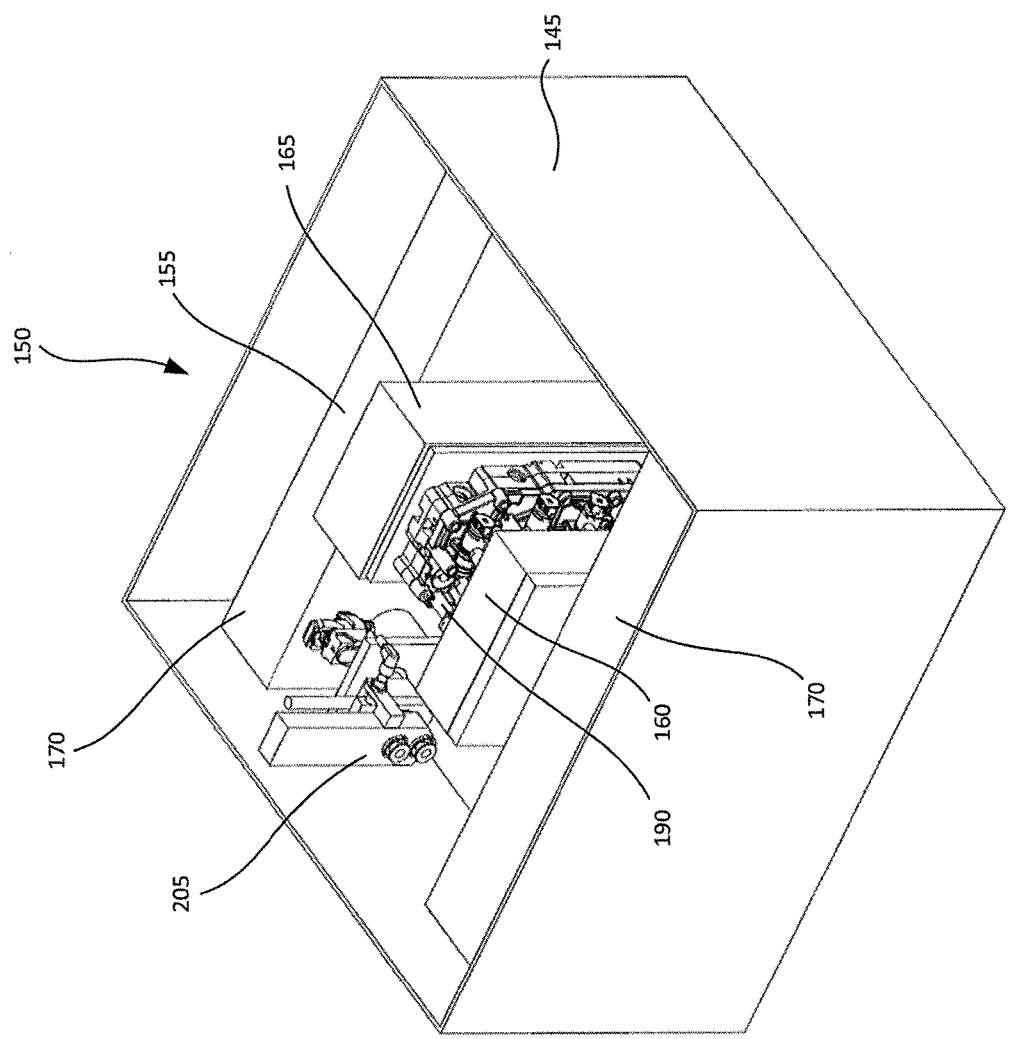
FIG. 20 illustrate a test station according to an embodiment.
Figure 21:
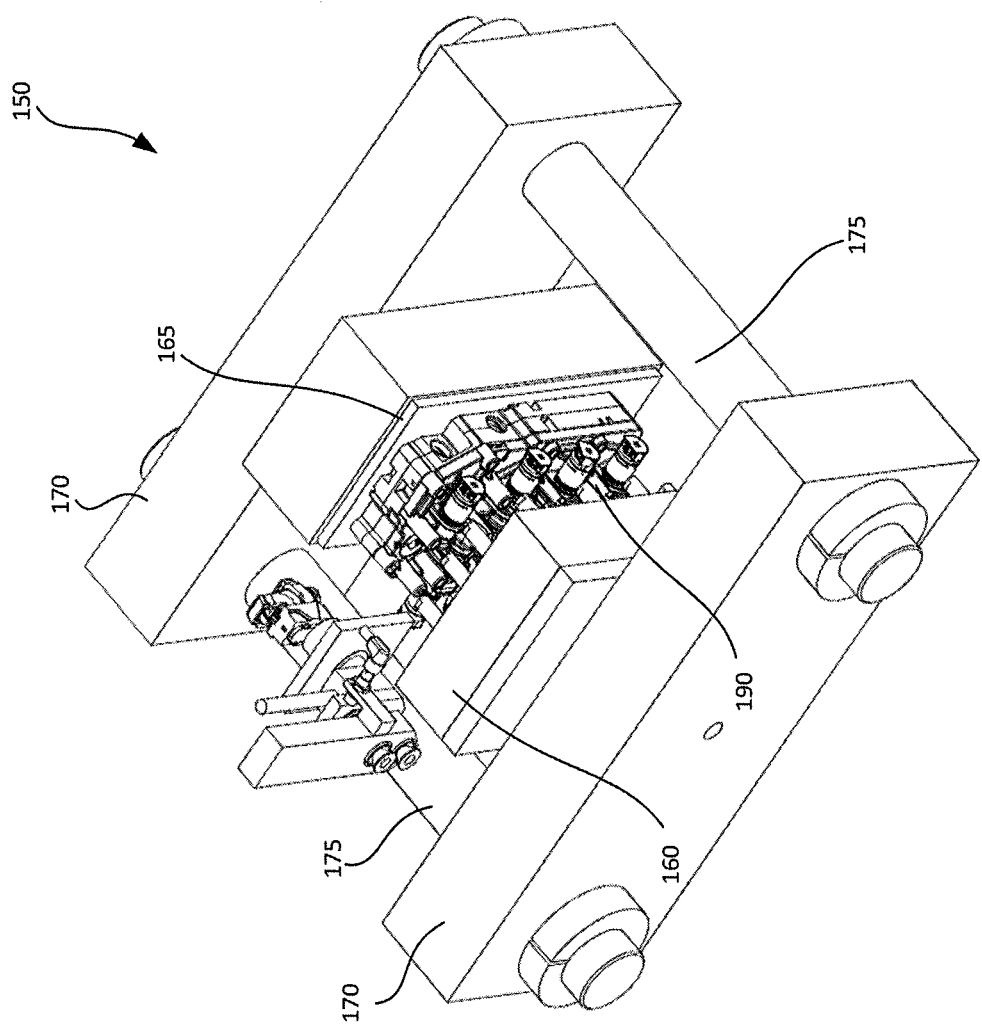
FIG. 21 illustrates a clamping mechanism of the test station of FIG. 20.
Figure 22:
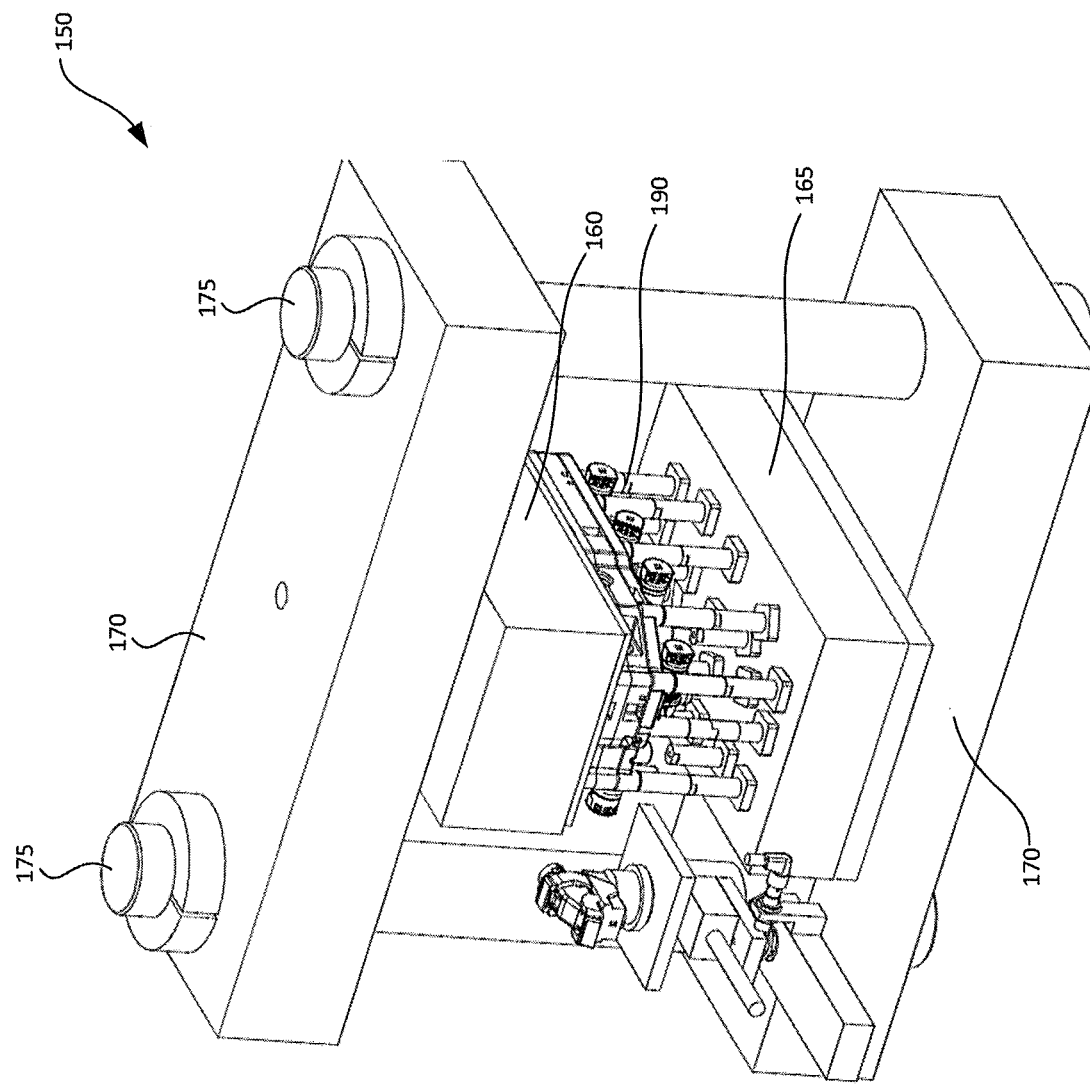
FIG. 22 illustrates a side view of the clamping mechanism of FIG. 21.

FIGS. 20 to 22 illustrate further detail for an embodiment of the test station 110. Each test station 110 includes a container 145 and at least one clamping mechanism 150. FIGS. 21 and 22 illustrate the clamping mechanism 150 removed from the container 145. As noted above, the clamp plates 170 (sometimes referred to as fixture plates) are held in fixed orientation while the part 200 is loaded between the clamping module 160 and the seal manifold 165 (sometimes referred to as a seal plate). The clamping module 160 is then activated such that pistons 190 move forward to hold the part against the seal manifold 165 with appropriate force placed in the correct positions to hold the part in place during testing. The hydraulic force for the pistons 190 is provided by hydraulic cables or piping (not shown) that enter the clamping module 160 and drive the pistons 190. In other embodiments, the pistons 190 may be driven by another power source such as pneumatic or electrically driven pistons or the like.

It is intended for the part 200 to be loaded in a vertical position, similar to a "toaster" type insertion into the clamping mechanism 150. A connector slide 205 advances making electrical connection. In some cases, the clamping module 160 and seal manifold 165 are configured to be removable from the clamping frame 155 and quickly replaced.

Figure 23:
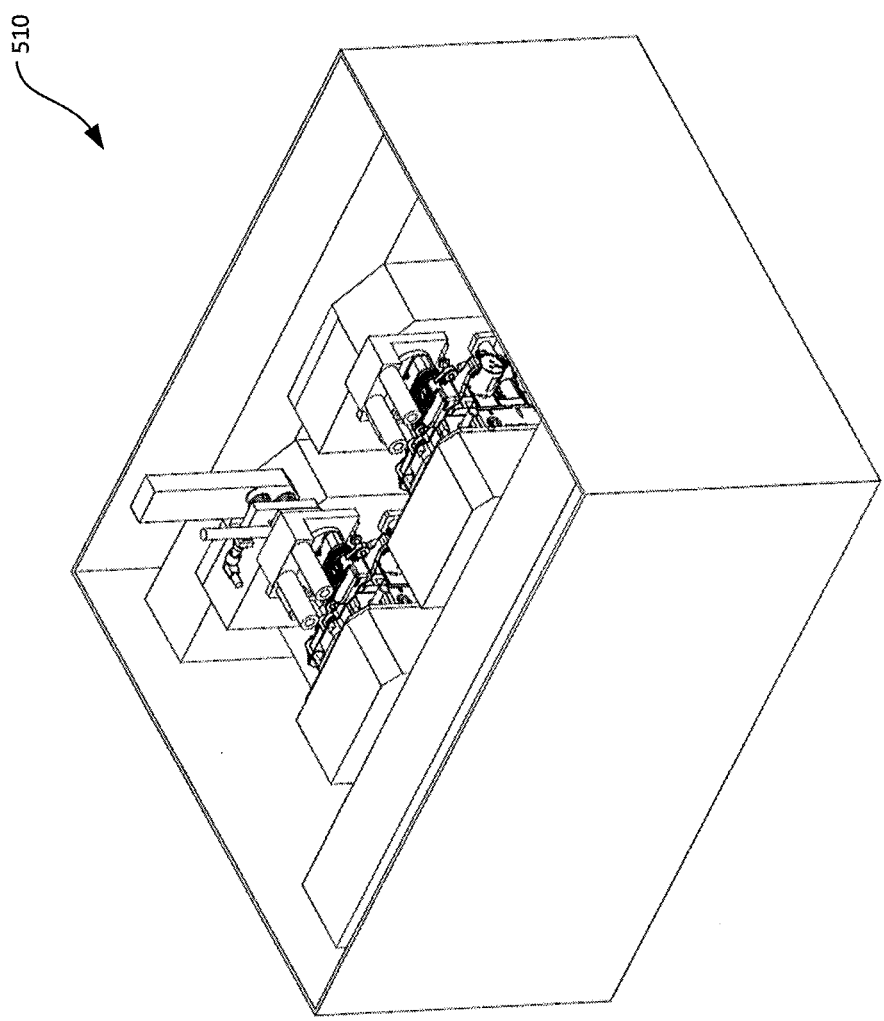
FIG. 23 illustrates another embodiment of the test station.
Figure 24:
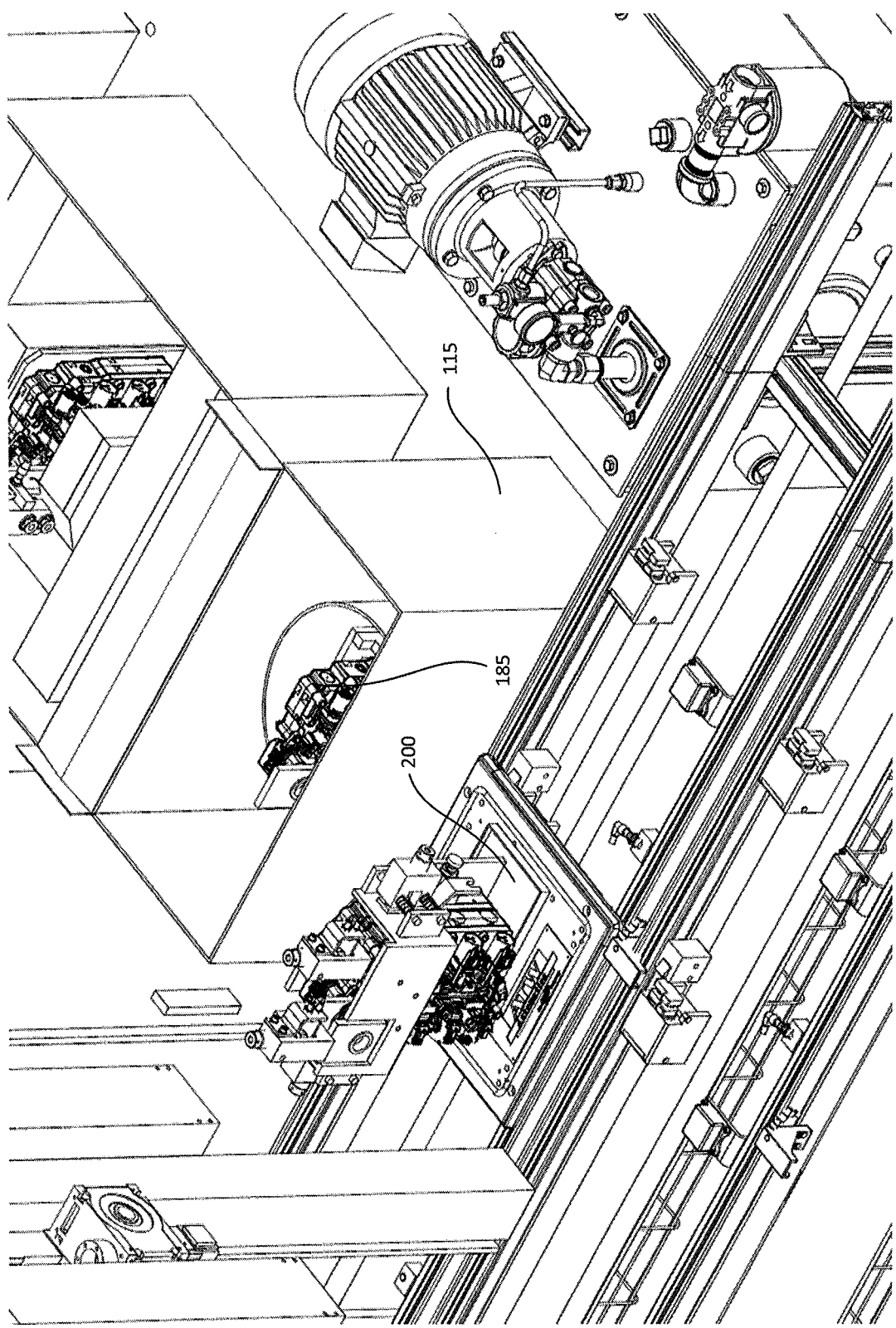
FIG. 24 illustrates an embodiment of the cleaning station.

FIG. 23 illustrates an embodiment of the test station 510 that is configured to hold two parts 200 (same type or different type). The part 200 may be held at either the same time or as required based on manufacturing need. This type of test station 510 could be used with the systems 500 and 600 described above.

Figure 25:
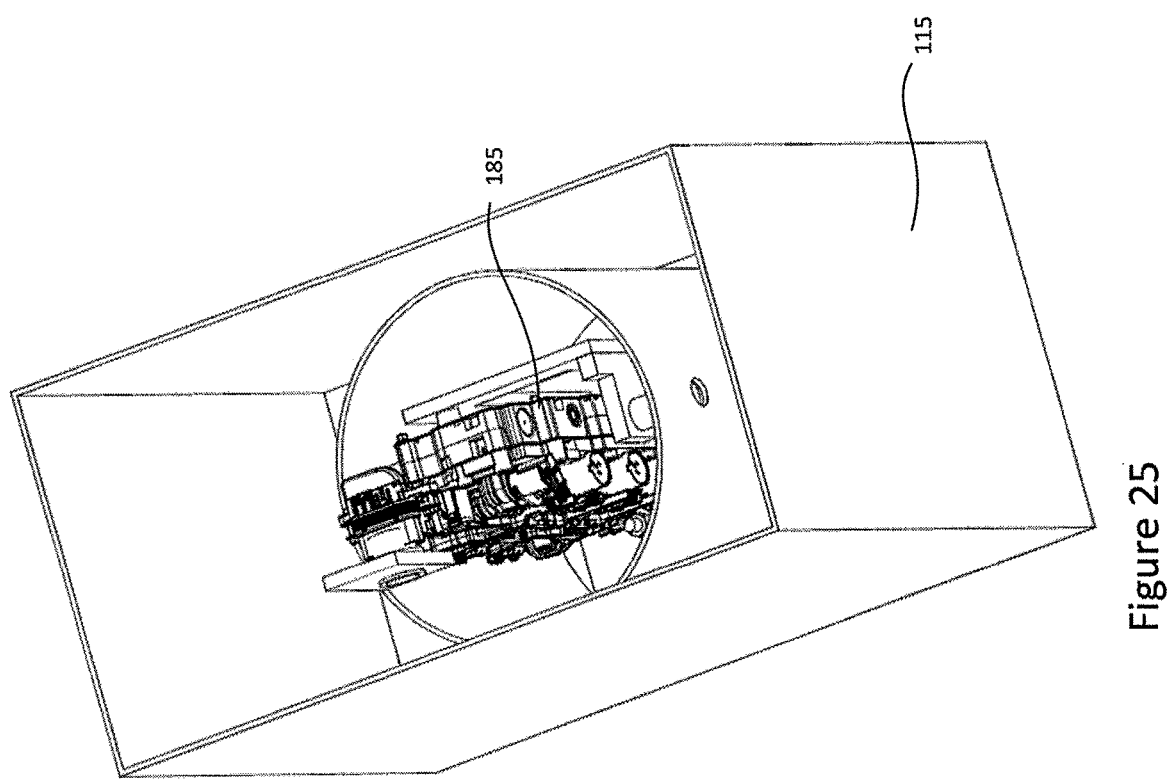
FIG. 25 illustrates a top perspective view of the cleaning station shown in FIG. 24.
Figure 26B:
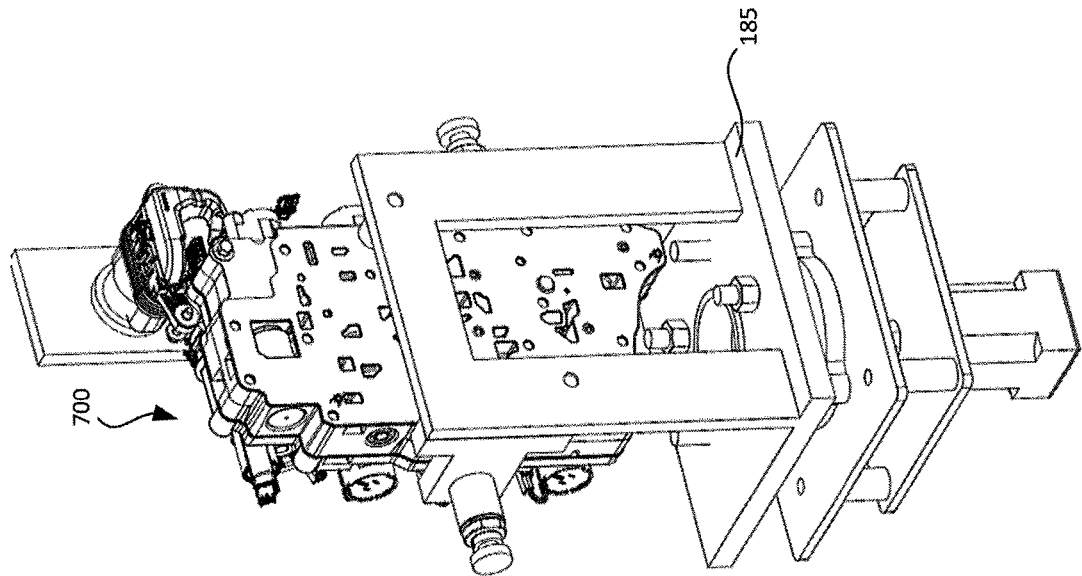
FIGS. 26A and 26B illustrate an embodiment of a spinner in the cleaning station with attached part.
Figure 26A:
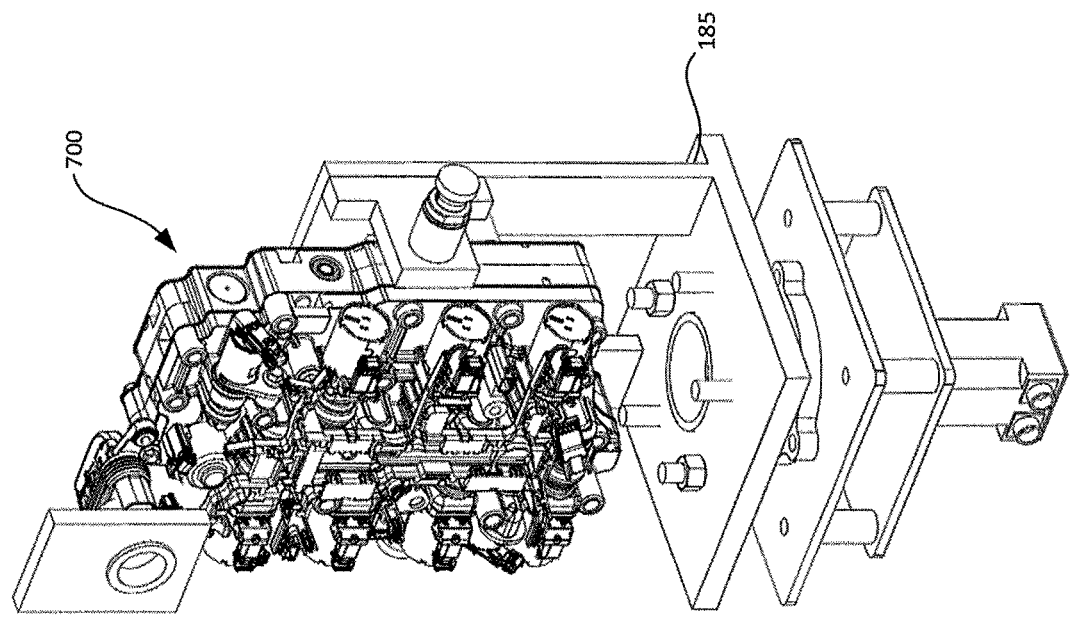

FIGS. 24 to 26B illustrate further detail of an embodiment of the cleaning station 115. In particular, FIGS. 25 and 26A and 26B illustrate a spinning mechanism 185 configured to receive, hold and spin a part to remove excess liquid. In some cases, the spinning mechanism may be drum that is spun by a motor. Similar to the pallet having a lock/release mechanism, the spinning mechanism 185 also includes a lock/release mechanism and interacts with the gripper to maintain part orientation and control.

Figure 27:
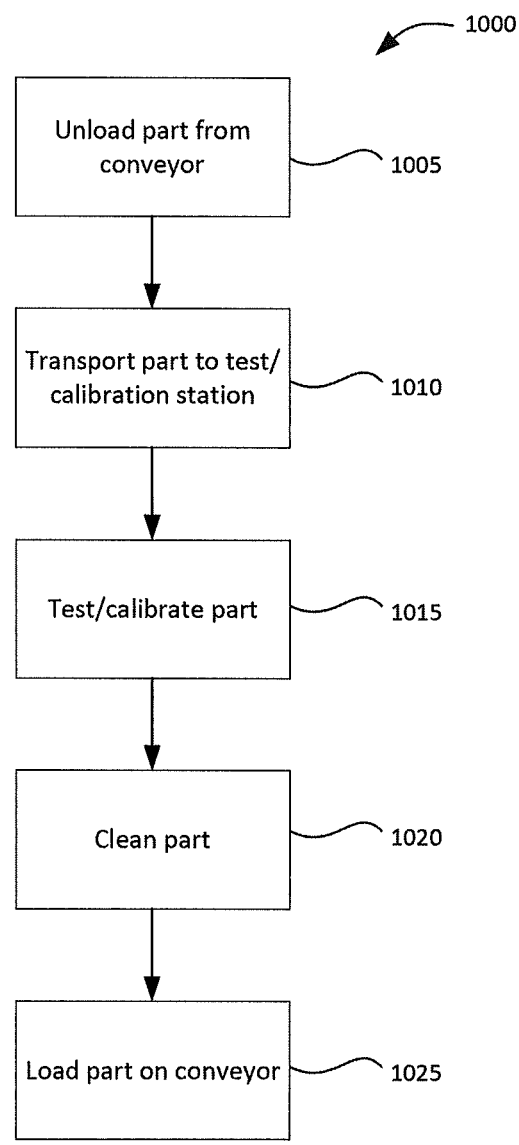
FIG. 27 is a flow chart illustrating an embodiment of a method for testing and calibration.

FIG. 27 illustrates a method 1000 for testing. At 1005, the part 200, for example a transmission control assembly or other part to be tested or calibrated arrives at the load/unload station of the system.

At 1010, the robotic module removes the part from the load/unload station and transports the part to the test station while maintaining or orienting the part in a generally vertical or upright orientation. The robotic module may include at least one moving mechanism with a gripper that grips the part to transport the part 200 to the test station.

At 1015, the part 200 is tested in the test station. The part 200 is placed into a clamping mechanism of the test station in a vertical orientation. The clamping mechanism is then operated to apply pressure to the part 200 during testing (e.g. pressure may be applied horizontally, on a generally horizontal plane). In cases where the part is tested in a wet environment, for example, when submerged in oil, the test station may already contain oil or be filled with oil in order to carry out the test, which may include calibration. Once the test and/or calibration is complete, the part is removed by the robotic module.

At 1020, the part 200 may be cleaned at a cleaning station. In cases where the part 200 was tested in a wet environment, for example, when submerged in oil, the part 200 may be cleaned at the cleaning station to remove excess liquid from the part 200. In some cases, the part 200 may be cleaned by a spinning mechanism housed within the cleaning station.

At 1025, the part 200 is transported by the robotic mechanism to the load/unload station in order to be returned to the conveyor.

Figure 28:
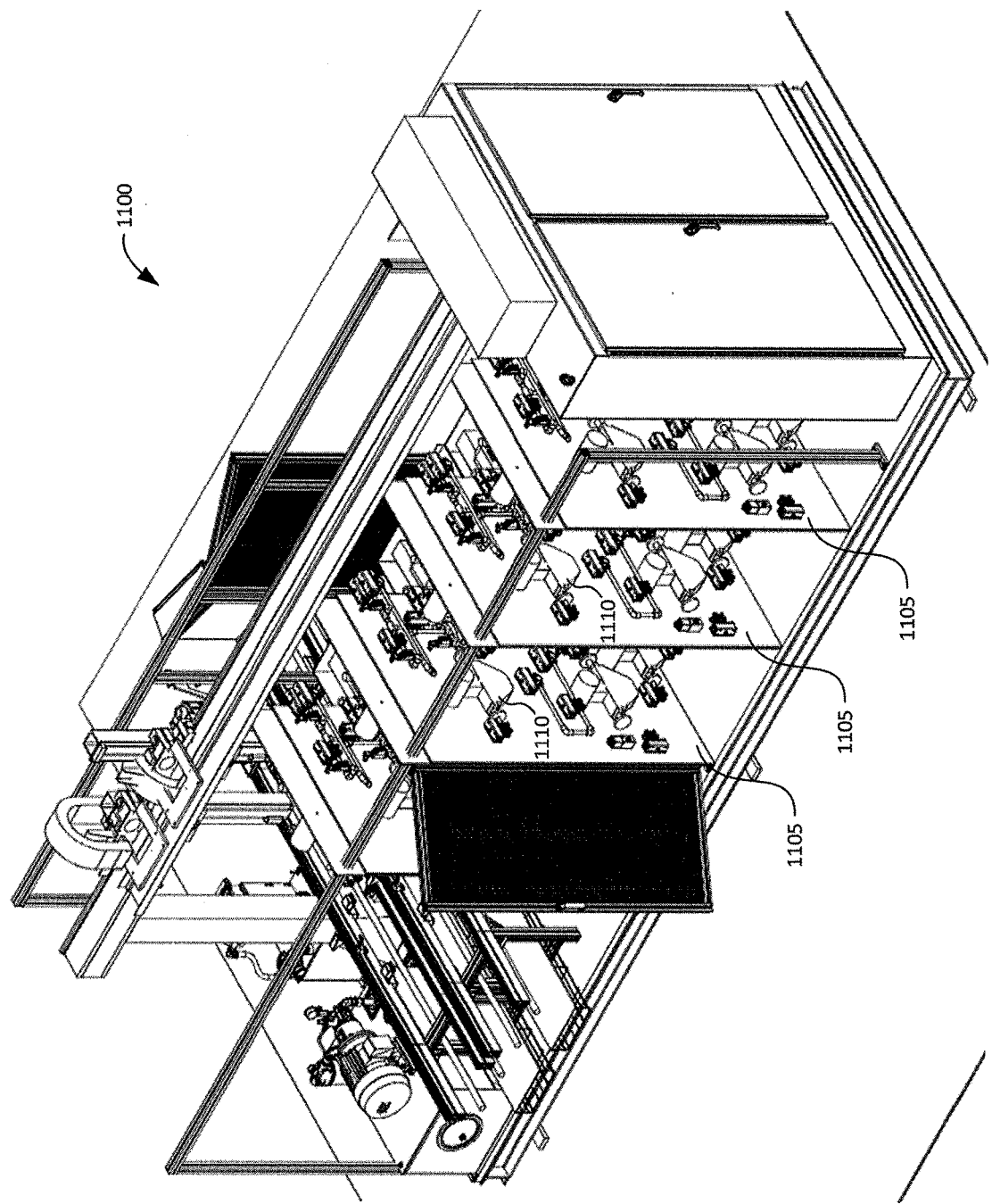
FIG. 28 illustrates a rear perspective view of a further embodiment of a system for testing and calibration.
Figure 29:
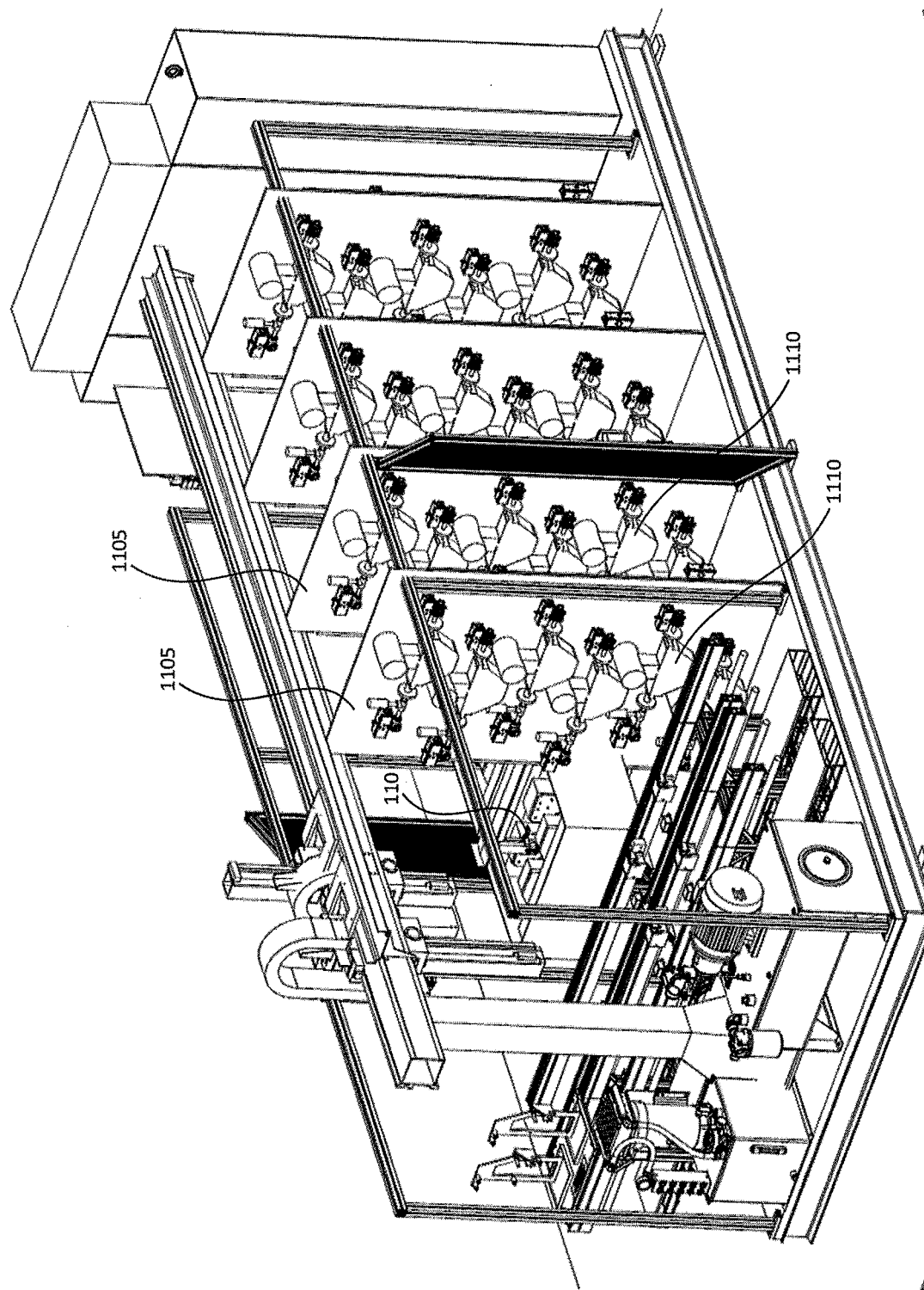
FIG. 29 illustrates a front right perspective view of the embodiment of the system of FIG. 28.
Figure 30:
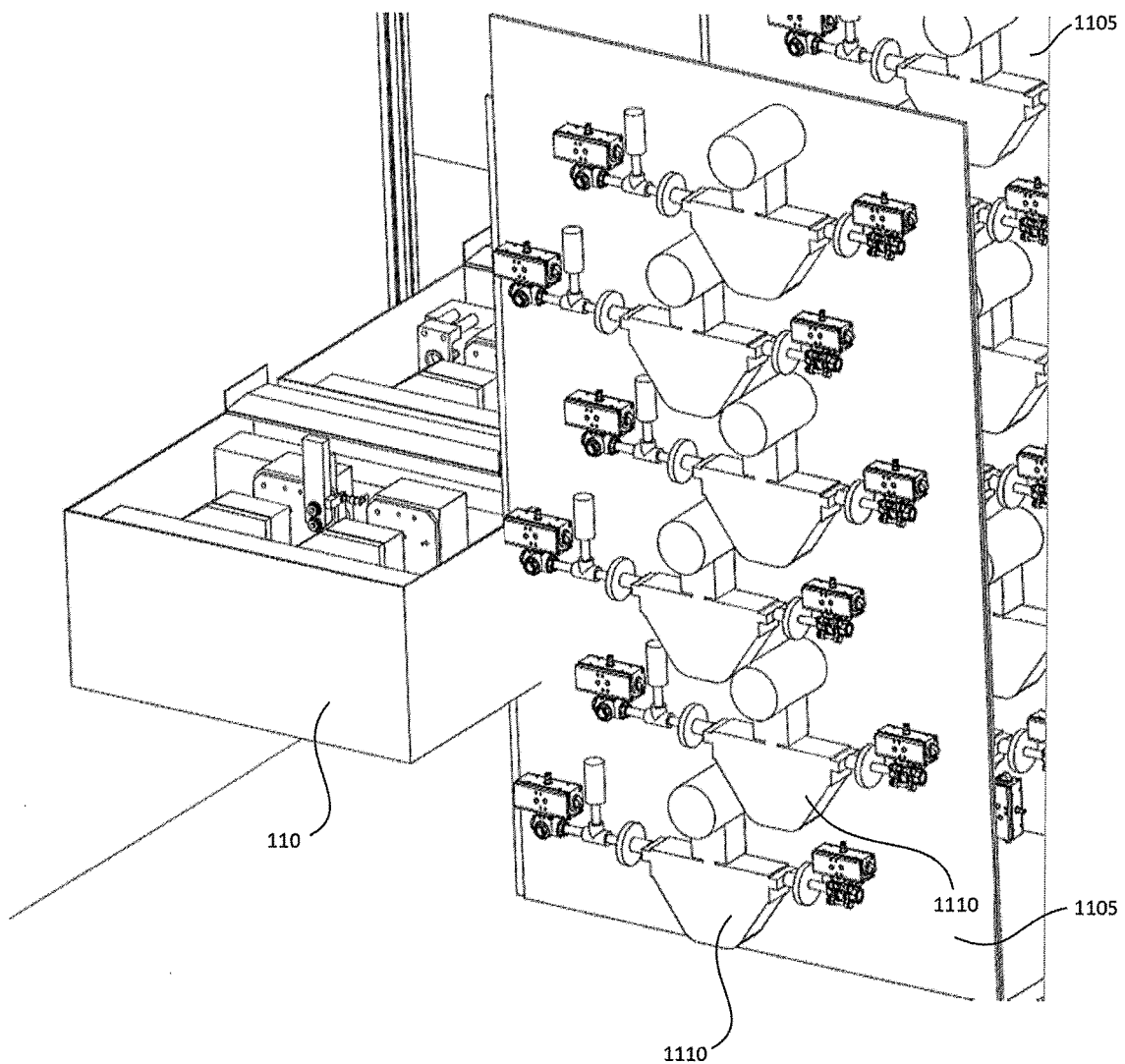
FIG. 30 illustrates a combined test panel and a test station.

FIGS. 28 and 29 illustrate yet another embodiment of a system 1100 for testing and calibration of a part 200. In this embodiment, the system 1100 is generally similar to the system 600 of FIG. 15. One difference is that the plurality of test panels 1105 are configured to connect with the test stations, for example test stations 110. In particular, a test valve 1110 can be configured to connect to the test station 110. The test panels 1105 may be located proximate to the test stations which may reduce the required floor space around the system 100. The test panels 1105 may be removed together with the test stations when a repair or replacement is needed. In particular, the test station and test panel can be slidably removed, which may allow for a replacement unit to be inserted more quickly and efficiently. The test station remains engaged with the test panel and a new part or repair can be completed outside the system while allowing the remaining test stations to continue production. As shown in FIG. 30, the test panels 1105 may include a plurality of test valves 1110, which may be mounted to either or both sides of the test panel. This may allow easier changeover during repair replacement and/or provide greater throughput.

Figure 31:
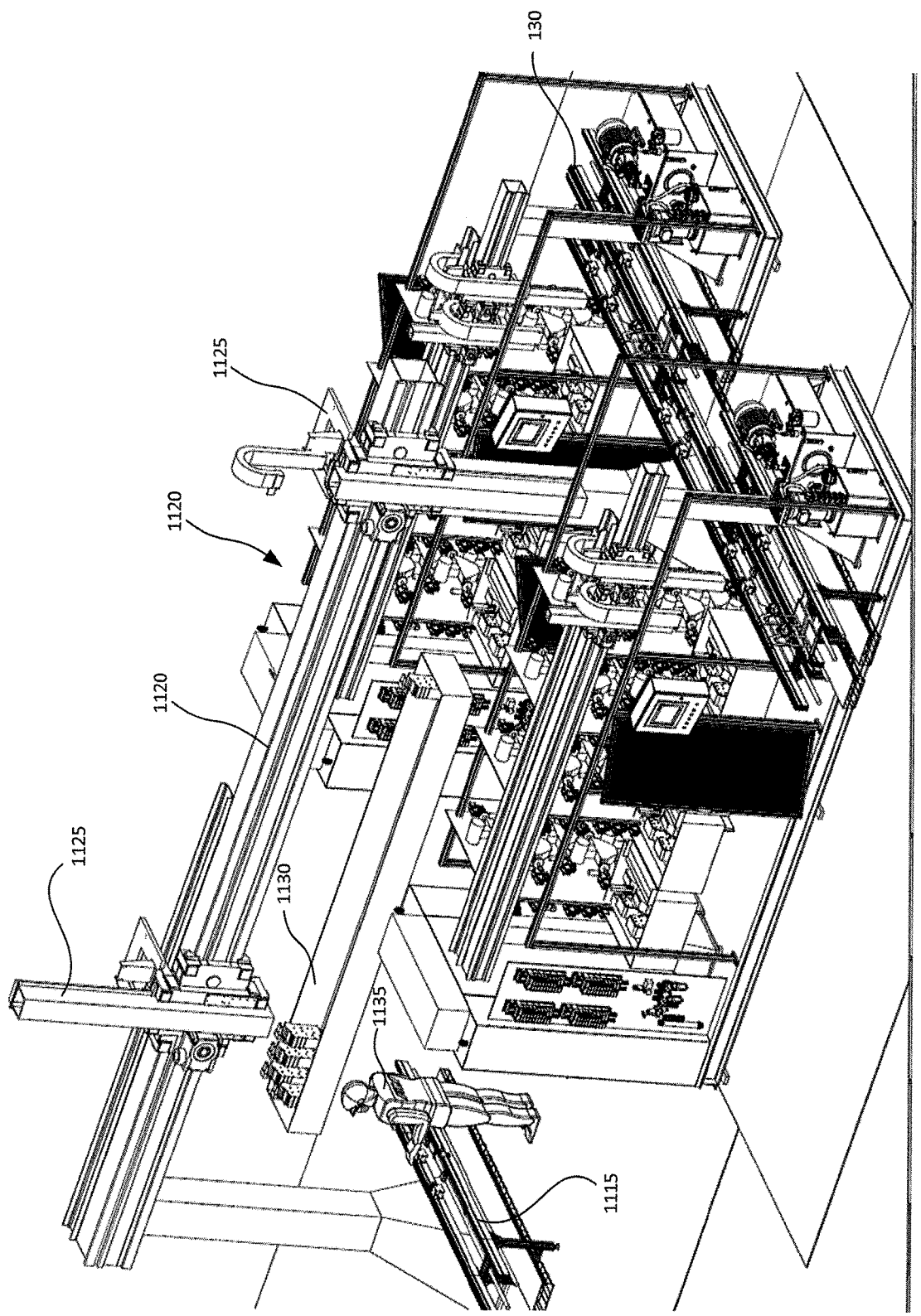
FIG. 31 illustrates an embodiment of a system for testing and calibration as included in an assembly line.

FIG. 31 illustrates the system 1100 as included as a component in an assembly line 1115. After processing by the system 1100, the part 200 is unloaded onto an unload conveyor 130. A transfer gantry 1120 is able to retrieve the part 200 and transfer it to the assembly line 1115. The transfer gantry 1120 includes a "Z" axis picker 1125 which may pick the part off the pallet and transfer the part 200 to a buffering area 1130. The buffering area 1130 may allow for further drying time for the part 200 (e.g. if the part 200 was processed in fluid). The "Z" axis picker 1125 may then pick parts 200 out of the buffering area and present the part directly in front of an assembly line operator 1135 and the assembly line operator 1135 to place the part 200 on the assembly line 1115. In some cases, there may be at least two "Z" axis pickers 1125, for example, one to move the part 200 from the unload conveyor 130 to the buffering area 1130 and a second to move the part 200 from the buffering area 1130 to the assembly line 1115. In some cases, the "Z" axis picker 1125 may move the part directly to the assembly line 1115.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

What is claimed is:

1. A system for testing or calibrating a manufactured part, the system comprising:
a plurality of test stations, each test station comprising a container and a clamping mechanism, wherein the container is configured to hold a liquid and the clamping mechanism is configured to receive the manufactured part in a vertical orientation and clamp the manufactured part horizontally with sufficient force to withstand a predetermined pressure to be placed on the manufactured part while submerged in the liquid, wherein the clamping mechanism comprises:
a clamp frame comprising:
two clamp plates;
a plurality of clamp bars configured to securely hold the clamp plates at a distance relative to each other;
a seal manifold provided on one of the two clamp plates; and
a clamping module, located opposite the seal manifold on another of the two clamp plates, wherein the clamping module comprises:
a plurality of pistons to hold the manufactured part against the seal manifold for a test operation; and
at least one cleaning station comprising a spin mechanism for spinning the manufactured part to remove excess liquid; and
a robotic system for moving manufactured parts to and from the plurality of test stations and to and from the at least one cleaning station.

2. A system according to claim 1, wherein the robotic system comprises:
   a gantry located above the plurality of test stations;
   a robotic module comprising:
      at least one moving mechanism configured to move along the gantry; and
      a robot gripper attached to each moving mechanism and configured to grip and transport the manufactured part.

3. A system according to claim 2, wherein the robot gripper is configured to maintain the vertical orientation of the manufactured part.

4. A system according to claim 2, further comprising a pallet for carrying the part and wherein the robot gripper comprises a lock/release mechanism configured to interact with the pallet.

5. A system according to claim 1, wherein the robotic system comprises:
   a floor mount; and
   a robotic arm attached to the floor mount, wherein the robotic arm moves the manufactured part to and from the plurality of test stations.

6. A system according to claim 1, wherein the spinning mechanism maintains the manufactured part in a vertical orientation.

7. A system according to claim 1 further comprising:
   a plurality of test panels, wherein each of the plurality of test panels engage with one of the plurality of test stations such that each of the engaged test panels and test stations can be slidably removed from the system.

8. A method for testing or calibrating a manufactured part, the method comprising:
   receiving the manufactured part from a conveyor;
   transporting the manufactured part to a test station while orienting the manufactured part in a vertical orientation;
   inserting the manufactured part in a clamping mechanism in the test station while maintaining the manufactured part in a vertical orientation, wherein the test station comprises a liquid;
   applying pressure to the manufactured part via the clamping mechanism, wherein the pressure is applied in a horizontal direction;
   testing or calibrating the manufactured part, while maintaining the manufactured part in a vertical orientation and while under pressure and inserted into the liquid;
   releasing the pressure and removing the manufactured part from the clamping mechanism; and
   returning the manufactured part to the conveyor.

9. A method according to claim 8, the method further comprising cleaning the part at a cleaning station by spinning the part to remove excess liquid.

10. A system for testing or calibrating manufactured parts under pressure, the system comprising:
    a plurality of test stations, each test station comprising:
    a clamping mechanism configured to receive a manufactured part in a vertical orientation and clamp the manufactured part horizontally with sufficient force to withstand a predetermined pressure to be placed on the manufactured part;
    a liquid into which the manufactured part is submerged during testing; and
    a robotic system for moving individual manufactured parts to and from the plurality of test stations.

11. A system according to claim 10, wherein the clamping mechanism comprises:
    a clamp frame comprising:
       two clamp plates;
       a plurality of clamp bars configured to securely hold the clamp plates at a distance relative to each other;
       a seal manifold provided on one of the two clamp plates; and
    a clamping module, located opposite the seal manifold on another of the two clamp plates, wherein the clamping module comprises:
    a plurality of pistons to hold the manufactured part against the seal manifold for the test operation.

12. A system according to claim 10, wherein the robotic system comprises:
    a gantry located above the plurality of test stations;
    a robotic module comprising:
       at least one moving mechanism configured to move along the gantry; and
       a robot gripper attached to each moving mechanism and configured to grip and transport the manufactured part.

13. A system according to claim 12, wherein the robot gripper is configured to maintain the vertical orientation of the manufactured part.

14. A system according to claim 12, further comprising a pallet for carrying the manufactured part and wherein the robot gripper comprises a lock/release mechanism configured to interact with the pallet.

15. A system according to claim 10, wherein the robotic system comprises:
    a floor mount; and
    a robotic arm attached to the floor mount, wherein the robotic arm moves the manufactured part to and from the plurality of test stations.

16. A system according to claim 10, further comprising at least one cleaning station comprising a spin mechanism for spinning.

17. A system according to claim 16, wherein the spinning mechanism maintains the manufactured part in a vertical orientation.

18. A system according to claim 10 further comprising:
    a plurality of test panels, wherein each of the plurality of test panels engage with one of the plurality of test stations such that each of the engaged test panels and test/calibration stations can be slidably removed from the system.

* * * * *